(12) United States Patent
Heagle et al.

(10) Patent No.: US 9,474,654 B2
(45) Date of Patent: *Oct. 25, 2016

(54) WOUND DRESSING OF CONTINUOUS FIBERS

(71) Applicant: Smith & Nephew, Inc., Memphis, TN (US)

(72) Inventors: David G. Heagle, Taunton, MA (US); Kevin Corley, Reading, MA (US); Kristin L. Watson, North Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/326,295

(22) Filed: Jul. 8, 2014

(65) Prior Publication Data

US 2014/0323997 A1    Oct. 30, 2014

Related U.S. Application Data

(63) Continuation of application No. 13/569,905, filed on Aug. 8, 2012, now Pat. No. 8,777,911, which is a continuation of application No. 12/537,284, filed on Aug. 7, 2009, now abandoned.

(60) Provisional application No. 61/147,179, filed on Jan. 26, 2009, provisional application No. 61/096,105, filed on Sep. 11, 2008, provisional application No. 61/188,370, filed on Aug. 8, 2008.

(51) Int. Cl.
*A61F 13/00* (2006.01)
*A61F 13/02* (2006.01)
*A61M 1/00* (2006.01)

(52) U.S. Cl.
CPC ... *A61F 13/00068* (2013.01); *A61F 13/00042* (2013.01); *A61F 13/00063* (2013.01); *A61F 13/02* (2013.01); *A61F 13/0216* (2013.01); *A61M 1/0088* (2013.01); *A61F 2013/0054* (2013.01); *A61F 2013/0057* (2013.01); *A61F 2013/00174* (2013.01);

(Continued)

(58) Field of Classification Search
CPC ............... A61F 13/00068; A61F 2013/00238
See application file for complete search history.

(56) References Cited

U.S. PATENT DOCUMENTS 3,026,874 A    3/1962  Stevens
3,367,332 A    2/1968  Groves (Continued)

FOREIGN PATENT DOCUMENTS

AU         674837 B2      1/1997
DE       41 11 122 A1     4/1993

(Continued)

OTHER PUBLICATIONS

U.S. Patent No. 6,216,701, Apr. 17, 2011, Heaton et al. (withdrawn).

(Continued)

*Primary Examiner* — Philip R Wiest
*Assistant Examiner* — Sara Sass
(74) *Attorney, Agent, or Firm* — Knobbe, Martens, Olson & Bear, LLP

(57) ABSTRACT

A method for treating a wound that includes incorporating a wound dressing comprising a plurality of fibers, each fiber having a length of at least two (2) inches, into a wound to cause the walls of the wound to remain apart and allow the wound to heal from the inside to the outside, and removing the wound exudate.

12 Claims, 12 Drawing Sheets

(52) U.S. Cl.
CPC ............... *A61F 2013/00238* (2013.01); *A61F 2013/00348* (2013.01); *A61F 2013/00357* (2013.01); *A61F 2013/00412* (2013.01); *A61F 2013/00519* (2013.01); *A61F 2013/00536* (2013.01); *A61F 2013/00557* (2013.01); *A61F 2013/00565* (2013.01); *A61F 2013/00842* (2013.01)

(56) References Cited

U.S. PATENT DOCUMENTS

| | | |
|---|---|---|
| 3,486,504 A | 12/1969 | Austin, Jr. |
| 3,568,675 A | 3/1971 | Harvey |
| 3,572,340 A | 3/1971 | Lloyd et al. |
| 3,712,298 A | 1/1973 | Snowdon et al. |
| 3,809,086 A | 5/1974 | Schachet et al. |
| 3,874,387 A | 4/1975 | Barbieri |
| 3,963,029 A | 6/1976 | Brooks |
| 3,972,328 A | 8/1976 | Chen |
| 3,980,166 A | 9/1976 | DeFeudis |
| 4,063,556 A | 12/1977 | Thomas et al. |
| 4,080,970 A | 3/1978 | Miller |
| 4,112,947 A | 9/1978 | Nehring |
| 4,112,949 A | 9/1978 | Rosenthal et al. |
| 4,136,696 A | 1/1979 | Nehring |
| 4,202,331 A | 5/1980 | Yale |
| 4,224,945 A | 9/1980 | Cohen |
| 4,228,798 A | 10/1980 | Deaton |
| 4,266,545 A | 5/1981 | Moss |
| 4,280,680 A | 7/1981 | Payne |
| 4,382,441 A | 5/1983 | Svedman |
| 4,510,802 A | 4/1985 | Peters |
| 4,524,064 A | 6/1985 | Nambu |
| 4,538,645 A | 9/1985 | Perach |
| 4,605,399 A | 8/1986 | Weston et al. |
| 4,655,754 A | 4/1987 | Richmond et al. |
| 4,665,909 A | 5/1987 | Trainor |
| 4,700,479 A | 10/1987 | Saito et al. |
| 4,710,165 A | 12/1987 | McNeil et al. |
| 4,738,257 A | 4/1988 | Meyer et al. |
| 4,743,232 A | 5/1988 | Kruger |
| 4,870,975 A | 10/1989 | Cronk et al. |
| 4,874,363 A | 10/1989 | Abell |
| 4,969,880 A | 11/1990 | Zamierowski |
| 4,990,137 A | 2/1991 | Graham |
| 4,997,438 A | 3/1991 | Nipper |
| 5,071,409 A | 12/1991 | Rosenberg |
| 5,100,395 A | 3/1992 | Rosenberg |
| 5,100,396 A | 3/1992 | Zamierowski |
| 5,106,629 A | 4/1992 | Cartmell et al. |
| 5,135,485 A | 8/1992 | Cohen et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,176,663 A | 1/1993 | Svedman et al. |
| 5,178,157 A | 1/1993 | Fanlo |
| 5,180,375 A | 1/1993 | Feibus |
| 5,195,977 A | 3/1993 | Pollitt |
| 5,238,732 A | 8/1993 | Krishnan |
| 5,261,893 A | 11/1993 | Zamierowski |
| 5,263,922 A | 11/1993 | Sova et al. |
| 5,399,418 A | 3/1995 | Hartmanns et al. |
| 5,484,427 A | 1/1996 | Gibbons |
| 5,527,293 A | 6/1996 | Zamierowski |
| 5,536,233 A | 7/1996 | Khouri |
| 5,549,584 A | 8/1996 | Gross |
| 5,588,958 A | 12/1996 | Cunningham et al. |
| 5,599,289 A | 2/1997 | Castellana |
| 5,624,374 A | 4/1997 | Von Iderstein |
| 5,636,643 A | 6/1997 | Argenta et al. |
| 5,645,081 A | 7/1997 | Argenta et al. |
| 5,678,564 A | 10/1997 | Lawrence et al. |
| 5,701,917 A | 12/1997 | Khouri |
| 5,733,305 A | 3/1998 | Fleischmann |
| 5,759,570 A | 6/1998 | Arnold |
| 5,779,657 A | 7/1998 | Daneshvar |
| 5,795,584 A | 8/1998 | Totakura et al. |
| 5,840,049 A | 11/1998 | Tumey et al. |
| 5,911,222 A | 6/1999 | Lawrence et al. |
| 5,944,703 A | 8/1999 | Dixon et al. |
| 5,960,837 A | 10/1999 | Cude |
| 6,010,524 A | 1/2000 | Fleischmann |
| 6,071,267 A | 6/2000 | Zamierowski |
| 6,117,111 A | 9/2000 | Fleischmann |
| 6,135,116 A | 10/2000 | Vogel et al. |
| 6,142,982 A | 11/2000 | Hunt et al. |
| 6,174,306 B1 | 1/2001 | Fleischmann |
| 6,203,563 B1 | 3/2001 | Fernandez |
| 6,235,302 B1 | 5/2001 | Mans et al. |
| 6,261,276 B1 | 7/2001 | Reitsma |
| 6,325,788 B1 | 12/2001 | McKay |
| 6,345,623 B1 | 2/2002 | Heaton et al. |
| 6,348,423 B1 | 2/2002 | Griffiths et al. |
| 6,395,955 B1 | 5/2002 | Roe et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,458,109 B1 | 10/2002 | Henley et al. |
| 6,488,643 B1 | 12/2002 | Tumey et al. |
| 6,500,112 B1 | 12/2002 | Khouri |
| 6,520,982 B1 | 2/2003 | Boynton et al. |
| 6,547,255 B1 | 4/2003 | Donaway et al. |
| 6,553,998 B2 | 4/2003 | Heaton et al. |
| 6,557,704 B1 | 5/2003 | Randolph |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,979,324 B2 | 12/2005 | Byvordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,052,167 B2 | 5/2006 | Vanderschuit |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,128,719 B2 | 10/2006 | Rosenberg |
| 7,128,735 B2 | 10/2006 | Weston |
| 7,144,390 B1 | 12/2006 | Hannigan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| 7,273,054 B2 | 9/2007 | Heaton et al. |
| 7,276,051 B1 | 10/2007 | Henley et al. |
| 7,279,612 B1 | 10/2007 | Heaton et al. |
| 7,316,672 B1 | 1/2008 | Hunt et al. |
| 7,338,482 B2 | 3/2008 | Lockwood et al. |
| 7,351,250 B2 | 4/2008 | Zamierowski |
| 7,361,184 B2 | 4/2008 | Joshi |
| 7,381,211 B2 | 6/2008 | Zamierowski |

(56) References Cited

U.S. PATENT DOCUMENTS

| | | | |
|---|---|---|---|
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,485,112 B2 | 2/2009 | Karpowicz et al. |
| 7,503,910 B2 | 3/2009 | Adahan |
| 7,524,315 B2 | 4/2009 | Blott et al. |
| 7,534,927 B2 | 5/2009 | Lockwood et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,708,724 B2 | 5/2010 | Weston |
| 7,722,582 B2 | 5/2010 | Lina et al. |
| 7,759,539 B2 | 7/2010 | Shaw et al. |
| 7,759,737 B2 | 7/2010 | Cho et al. |
| 7,775,998 B2 | 8/2010 | Riesinger |
| 7,779,625 B2 | 8/2010 | Joshi et al. |
| 7,794,438 B2 | 9/2010 | Henley et al. |
| 7,811,269 B2 | 10/2010 | Boynton et al. |
| 7,846,141 B2 | 12/2010 | Weston |
| 7,862,718 B2 | 1/2011 | Doyen et al. |
| 7,909,805 B2 | 3/2011 | Weston |
| 7,910,791 B2 | 3/2011 | Coffey |
| 7,922,703 B2 | 4/2011 | Riesinger |
| 7,964,766 B2 | 6/2011 | Blott et al. |
| 8,062,272 B2 | 11/2011 | Weston |
| 8,162,907 B2 | 4/2012 | Heagle |
| 8,241,261 B2 | 8/2012 | Randolph et al. |
| 8,298,200 B2 | 10/2012 | Vess et al. |
| 8,545,466 B2 | 10/2013 | Andresen et al. |
| 8,641,691 B2 | 2/2014 | Fink et al. |
| 8,777,911 B2 * | 7/2014 | Heagle et al. | 604/317 |
| 9,033,942 B2 | 5/2015 | Vess |
| 2001/0020145 A1 | 9/2001 | Satterfield |
| 2001/0031943 A1 | 10/2001 | Urie |
| 2001/0043943 A1 | 11/2001 | Coffey |
| 2002/0016577 A1 | 2/2002 | Ohmstede |
| 2002/0108614 A1 | 8/2002 | Schultz |
| 2002/0143286 A1 | 10/2002 | Tumey |
| 2002/0151836 A1 | 10/2002 | Burden |
| 2002/0161346 A1 | 10/2002 | Lockwood et al. |
| 2003/0078532 A1 | 4/2003 | Ruszczak et al. |
| 2003/0093041 A1 | 5/2003 | Risk, Jr. et al. |
| 2003/0181850 A1 | 9/2003 | Diamond et al. |
| 2003/0208149 A1 | 11/2003 | Coffey |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0054338 A1 | 3/2004 | Bybordi |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0082925 A1 | 4/2004 | Patel |
| 2004/0093026 A1 | 5/2004 | Weidenhagen et al. |
| 2004/0113309 A1 | 6/2004 | Thompson, Jr. et al. |
| 2004/0122434 A1 | 6/2004 | Argenta et al. |
| 2004/0167482 A1 | 8/2004 | Watson |
| 2004/0193218 A1 | 9/2004 | Butler |
| 2004/0241213 A1 | 12/2004 | Bray |
| 2004/0243073 A1 | 12/2004 | Lockwood et al. |
| 2004/0249353 A1 | 12/2004 | Risks, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0070835 A1 | 3/2005 | Joshi |
| 2005/0070858 A1 | 3/2005 | Lockwood et al. |
| 2005/0085795 A1 | 4/2005 | Lockwood et al. |
| 2005/0090787 A1 | 4/2005 | Risk, Jr. et al. |
| 2005/0101940 A1 | 5/2005 | Radl et al. |
| 2005/0107756 A1 * | 5/2005 | McCraw | A61M 27/00 604/317 |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0261643 A1 | 11/2005 | Bybordi et al. |
| 2006/0009744 A1 | 1/2006 | Erdman et al. |
| 2006/0015087 A1 | 1/2006 | Risk, Jr. et al. |
| 2006/0029650 A1 | 2/2006 | Coffey |
| 2006/0039742 A1 | 2/2006 | Cable, Jr. et al. |
| 2006/0040579 A1 * | 2/2006 | Sheldon | A61F 13/53 442/366 |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0149170 A1 | 7/2006 | Boynton et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0027414 A1 * | 2/2007 | Hoffman et al. | 602/2 |
| 2007/0032754 A1 | 2/2007 | Walsh |
| 2007/0032755 A1 | 2/2007 | Walsh |
| 2007/0032778 A1 | 2/2007 | Heaton et al. |
| 2007/0055209 A1 | 3/2007 | Patel et al. |
| 2007/0078432 A1 | 4/2007 | Halseth et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0219513 A1 | 9/2007 | Lina et al. |
| 2007/0225663 A1 | 9/2007 | Watt et al. |
| 2007/0233022 A1 | 10/2007 | Henley et al. |
| 2008/0011667 A1 | 1/2008 | Ruschke |
| 2008/0071235 A1 | 3/2008 | Locke et al. |
| 2008/0103462 A1 | 5/2008 | Wenzel et al. |
| 2008/0132819 A1 | 6/2008 | Radl et al. |
| 2008/0167593 A1 | 7/2008 | Fleischmann |
| 2008/0183233 A1 | 7/2008 | Koch et al. |
| 2008/0195017 A1 | 8/2008 | Robinson et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0234641 A1 | 9/2008 | Locke et al. |
| 2008/0306456 A1 | 12/2008 | Riesinger |
| 2009/0012501 A1 | 1/2009 | Boehringer et al. |
| 2009/0124988 A1 | 5/2009 | Coulthard |
| 2009/0131892 A1 | 5/2009 | Karpowicz et al. |
| 2009/0157016 A1 | 6/2009 | Adahan |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0264837 A1 | 10/2009 | Adahan |
| 2009/0287181 A1 * | 11/2009 | Kagan | A61B 17/12022 604/506 |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299303 A1 | 12/2009 | Seegert |
| 2009/0299306 A1 | 12/2009 | Buan |
| 2009/0299307 A1 | 12/2009 | Barta et al. |
| 2009/0299308 A1 | 12/2009 | Kazala et al. |
| 2009/0299340 A1 | 12/2009 | Kazala et al. |
| 2009/0299341 A1 | 12/2009 | Kazala et al. |

(56) References Cited

U.S. PATENT DOCUMENTS

| | | |
|---|---|---|
| 2009/0299342 A1 | 12/2009 | Cavanaugh, II et al. |
| 2009/0312728 A1 | 12/2009 | Randolph et al. |
| 2010/0036334 A1 | 2/2010 | Heagle et al. |
| 2010/0069850 A1 | 3/2010 | Fabo |
| 2010/0069885 A1 | 3/2010 | Stevenson et al. |
| 2010/0160901 A1 | 6/2010 | Hu et al. |
| 2010/0324510 A1 | 12/2010 | Andresen et al. |
| 2011/0028918 A1 | 2/2011 | Hartwell |
| 2011/0054421 A1 | 3/2011 | Hartwell |
| 2011/0172615 A2 | 7/2011 | Greener |
| 2011/0282309 A1 | 11/2011 | Adie et al. |
| 2013/0116635 A1 | 5/2013 | Fleischmann |
| 2013/0138054 A1 | 5/2013 | Fleischmann |

FOREIGN PATENT DOCUMENTS

| | | |
|---|---|---|
| DE | 43 06 478 | 9/1994 |
| DE | 295 04 378 U1 | 10/1995 |
| EP | 358 302 | 3/1990 |
| EP | 0 392 640 B1 | 6/1995 |
| EP | 0 441 418 B1 | 7/1995 |
| EP | 0 688 189 B2 | 12/1995 |
| EP | 0 465 601 B1 | 1/1997 |
| EP | 0 751 757 B1 | 1/1997 |
| EP | 0 853 950 | 7/1998 |
| EP | 0 777 504 B1 | 10/1998 |
| EP | 1 088 569 | 4/2001 |
| EP | 0 865 304 | 7/2001 |
| EP | 1 169 071 A1 | 1/2002 |
| EP | 1 219 311 | 7/2002 |
| EP | 1 897 569 | 8/2002 |
| EP | 0 853 950 | 10/2002 |
| EP | 0 708 620 B1 | 5/2003 |
| EP | 1 088 569 | 8/2003 |
| EP | 0 993 317 B1 | 9/2003 |
| EP | 1 440 667 A1 | 7/2004 |
| EP | 1 018 967 | 8/2004 |
| EP | 1 478 313 A2 | 11/2004 |
| EP | 1 487 389 A1 | 12/2004 |
| EP | 1 100 574 B1 | 2/2005 |
| EP | 1 440 667 | 3/2006 |
| EP | 1 284 777 B1 | 4/2006 |
| EP | 0 982 015 B1 | 8/2006 |
| EP | 0 620 720 B2 | 11/2006 |
| EP | 1 448 261 | 2/2007 |
| EP | 1 171 065 | 3/2007 |
| EP | 1 227 853 B1 | 1/2008 |
| EP | 1 476 217 | 3/2008 |
| EP | 1 909 863 A1 | 4/2008 |
| EP | 1 233 808 B1 | 7/2008 |
| EP | 1 977 776 A2 | 10/2008 |
| EP | 1 807 184 | 12/2008 |
| EP | 1 513 478 B1 | 12/2009 |
| EP | 1 905 465 B1 | 1/2010 |
| EP | 2 127 690 A2 | 3/2010 |
| EP | 2 172 164 | 4/2010 |
| EP | 2 319 550 | 5/2011 |
| EP | 1 578 477 B1 | 9/2011 |
| EP | 2 529 766 | 12/2012 |
| EP | 2 545 946 | 3/2013 |
| EP | 1 905 465 | 11/2013 |
| EP | 2 659 915 | 11/2013 |
| EP | 2 628 500 | 5/2014 |
| EP | 1 339 366 | 6/2014 |
| EP | 2 051 675 | 6/2014 |
| FR | 1163907 | 10/1958 |
| GB | 488 232 | 7/1938 |
| GB | 1 415 096 | 11/1975 |
| GB | 1 549 756 | 3/1977 |
| GB | 2 195 255 A | 4/1988 |
| GB | 2 235 877 A | 3/1991 |
| GB | 2 307 180 A | 5/1997 |
| GB | 2 329 127 A | 3/1999 |
| GB | 2 336 546 A | 10/1999 |
| GB | 2 307 180 B | 6/2000 |
| GB | 2 336 546 B | 6/2000 |
| GB | 2 344 531 A | 6/2000 |
| GB | 2 415 908 | 1/2006 |
| JP | 2002-508218 | 3/2002 |
| JP | 2004-509658 | 4/2004 |
| JP | 2005-536291 | 12/2005 |
| JP | 2008-080137 | 4/2008 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1990 |
| WO | WO 92/19313 | 11/1992 |
| WO | WO 93/09727 | 5/1993 |
| WO | WO 94/20041 | 9/1994 |
| WO | WO 96/05873 | 2/1996 |
| WO | WO 99/30661 | 6/1999 |
| WO | WO 00/21586 | 4/2000 |
| WO | WO 03/005943 | 1/2003 |
| WO | WO 03/018098 | 3/2003 |
| WO | WO 03/030966 | 4/2003 |
| WO | WO 03/045492 | 6/2003 |
| WO | WO 03/057070 | 7/2003 |
| WO | WO 03/057071 | 7/2003 |
| WO | WO 03/086232 | 10/2003 |
| WO | WO 03/092620 | 11/2003 |
| WO | WO 03/101508 | 12/2003 |
| WO | WO 2004/017883 | 3/2004 |
| WO | WO 2004/018020 | 4/2004 |
| WO | WO 2005/009488 | 2/2005 |
| WO | WO 2005/016179 | 2/2005 |
| WO | WO 2005/061025 | 7/2005 |
| WO | WO 2005/123170 | 12/2005 |
| WO | WO 2006/015599 | 2/2006 |
| WO | WO 2006/052338 | 5/2006 |
| WO | WO 2006/052745 | 5/2006 |
| WO | WO 2006/052839 | 5/2006 |
| WO | WO 2006/105892 | 10/2006 |
| WO | WO 2007/006306 | 1/2007 |
| WO | WO 2007/013064 | 2/2007 |
| WO | WO 2007/019038 | 2/2007 |
| WO | WO 2007/085396 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2008/008032 | 1/2008 |
| WO | WO 2008/012278 | 1/2008 |
| WO | WO 2008/020862 | 2/2008 |
| WO | WO 2008/027449 | 3/2008 |
| WO | WO 2008/043067 | 4/2008 |
| WO | WO 2008/048481 | 4/2008 |
| WO | WO 2008/100437 | 8/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/141470 | 11/2008 |
| WO | WO 2009/002260 | 12/2008 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/124100 | 10/2009 |
| WO | WO 2009/126103 | 10/2009 |
| WO | WO 2009/137194 | 11/2009 |
| WO | WO 2009/140376 | 11/2009 |
| WO | WO 2009/141820 | 11/2009 |
| WO | WO 2009/145894 | 12/2009 |
| WO | WO 2009/146396 | 12/2009 |
| WO | WO 2009/158125 | 12/2009 |
| WO | WO 2009/158126 | 12/2009 |
| WO | WO 2009/158127 | 12/2009 |
| WO | WO 2009/158128 | 12/2009 |
| WO | WO 2009/158129 | 12/2009 |
| WO | WO 2010/014177 | 2/2010 |
| WO | WO 2010/017437 | 2/2010 |
| WO | WO 2010/033271 | 3/2010 |

(56) References Cited

FOREIGN PATENT DOCUMENTS

| | | |
|---|---|---|
| WO | WO 2010/033272 | 3/2010 |
| WO | WO 2010/033769 | 3/2010 |
| WO | WO 2010/042240 | 4/2010 |
| WO | WO 2010/051073 | 5/2010 |
| WO | WO 2010/059712 | 5/2010 |
| WO | WO 2010/059730 | 5/2010 |
| WO | WO 2010/078166 | 7/2010 |
| WO | WO 2010/147533 | 12/2010 |
| WO | WO 2011/049562 | 4/2011 |
| WO | WO 2011/100851 | 8/2011 |
| WO | WO 2011/115908 | 9/2011 |
| WO | WO 2012/142002 | 10/2012 |
| WO | WO 2012/166428 | 12/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2013/043972 | 3/2013 |
| WO | WO 2013/123005 | 8/2013 |
| WO | WO 2014/066057 | 5/2014 |
| WO | WO 2014/043238 | 9/2014 |
| WO | WO 2014/158526 | 10/2014 |

OTHER PUBLICATIONS

U.S. Patent No. 7,186,244, Mar. 6, 2007, Hunt et al. (withdrawn).
International Search Report and Written Opinion, International Application No. PCT/US2009/053081, dated Sep. 24, 2009.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Bjorn, et al., "Irrigation Treatment in Split-thickness Skin Grafting of Intractable Leg Ulcers," Scand J Plast Reconstr Surg 19: 211-213,1985.
Chardack, et al., "Experimental studies on Synthetic Substitutes for Skin and Their Use in the Treatment of Burns," vol. 155, No. 1 (128-136), 1961.
Chariker, M.E., et al, "Effective Management of Incisional and Cutaneous Fistulae with Closed Suction Wound Drainage," Contemporary Surgery. Jun. 1989, pp. 59-63, vol. 34 USA.
Fleischmann, "Vacuum Sealing for Treatment of Problematical Wounds", University Surgical Clinic and Polyclinic—Accident Surgery Department, WundForum Spezial—IHW 94.
Fleischmann, et al., Vacuum Sealing: Indication, Technique and Results, Emr J Orthop Surg Tramatol (1995) 5:37-40.
Gorica Zivadinovic, et al., "Vacuum Therapy in the Treatment of Peripheral Blood Vessels," Conference Papers of the 5th Timok Medical Days, Majdanpek, 1986 (161-164).
Jeter, Katherine F., et al., "Managing Draining Wounds and Fistulae: New and Established Methods", Chronic Wound Care, 1990, pp. 240-246.
Kostiuchenok, et al., "The Vacuum Effect in the Surgical Treatment of Purulent Wounds," Russian Journal: Vestnik Khirurgii, Sep. 1986 (18-21).
Meyer, MD., et al., "In Surgery, Medicine and the Specialties a Manual of its Practical Application", Bier's Hyperemic Treatment, Second Revised Edition, W.B. Saunders Company, 1909.
Mulder, GD, et al., "Clinicians' Pocket Guide to Chronic Wound Repair," Wound Healing Publications Second Edition, 1991.
Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (323-326).
Sandén, Göran MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).
Stoll, "Energetic Remedies—Cupping: Healing Within a Vacuum," https:I/www.suite101.com/article.cfm/ energetic)remedies/74531, Apr. 13, 2005.
Svedman, "A Dressing Allowing Continuous Treatment of a Biosurface," IRCS Medical Science: Biomedical Technology; Clinical Medicine; Surgery and Transplantation, 7, 221 (1979).
Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Svedman, et al., "Staphylococcal Wound Infection in the Pig: Part I. Course," Annals of Plastic Surgery, vol. 23, No. 3, Sep. 1989 (212-218).
Teder, et al., "Continuous Wound Irrigation in the Pig," Journal of Investigative Surgery, vol. 3 (399-407).
Usupov, et al., "Active Wound Drainage," Russian Journal: Vestnik Khirugii, 1987, Apr. (42-45).
Yu A. Davydov, et al., "Bacteriological and Cylological Assessment of Vacuum Therapy of Purulent Wounds", Vestnik Khirurgii, Oct. 1988 (48-52).
Yu A. Davydov, et al., "Concepts for Clinical Biological Management of the Wound Process in the Treatment of Purulent Wounds Using Vacuum Therapy," Vestnik Khirurgii, Feb. 1991, 132-135).
Yu A. Davydov, et al., "Vacuum Therapy in the Treatment of Purulent Lactation Mastitis," Russian Journal: Vesnik Khirurgii, Sep. 1986 (66-70).
Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.
Kendall ULTEC Hydrocolloid Dressing (4"x4"), product ordering page, web page downloaded Jul. 13, 2014.
Protz, Kerstin: "Modern Wundauflagen unterstutzen Heilungsprozess", Wundversorgung: Indikation and Anwendung, Geriatrie Journal Apr. 2005, pp. 3333-3339.
Pentair Pool Products, 2000 Series Stainless Steel D. E. Filters (2006).

* cited by examiner

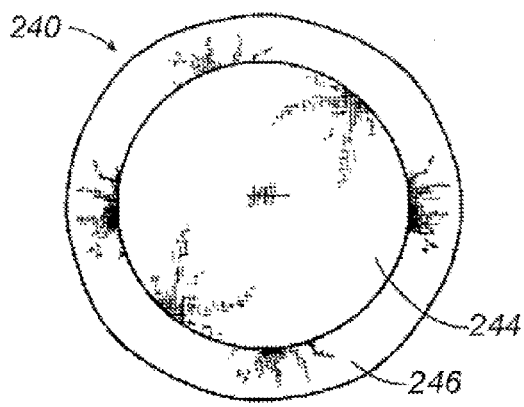
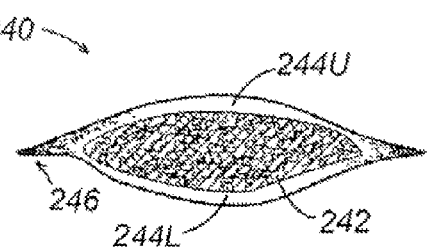
*FIG. 7A*
*FIG. 7B*
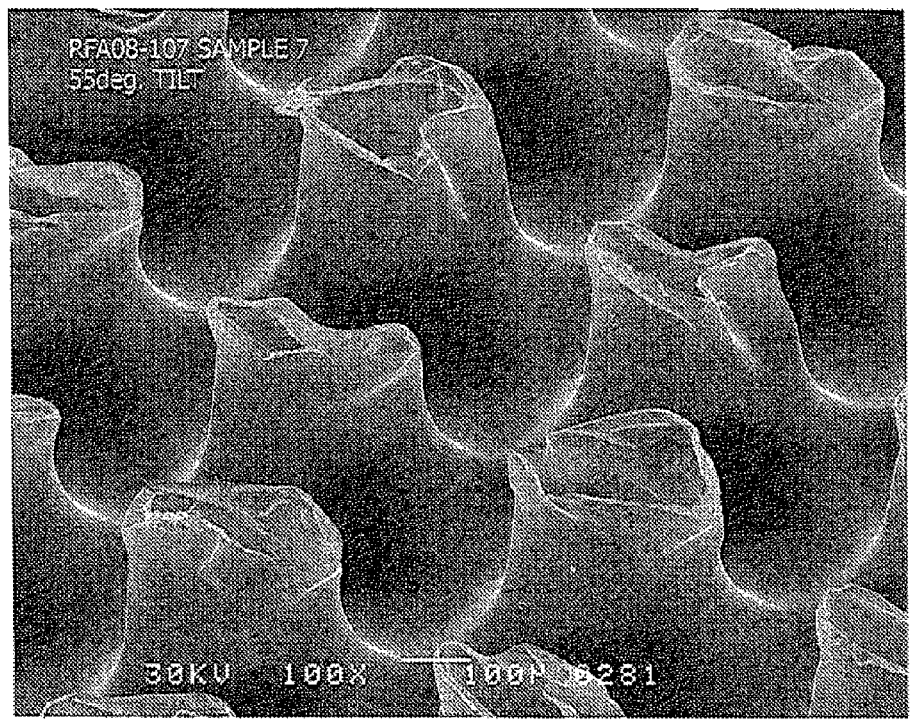
*FIG. 7C*

FIG. 10A    FIG. 10B

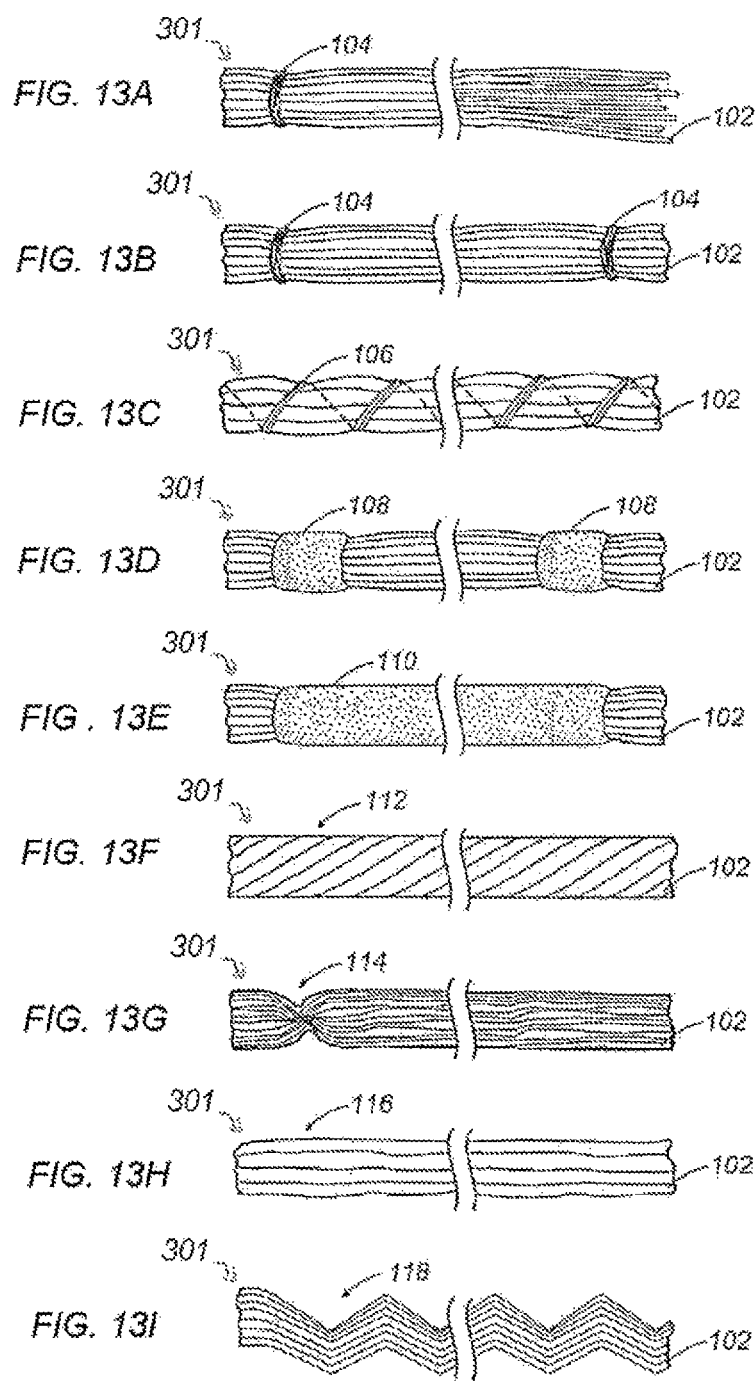

WOUND DRESSING OF CONTINUOUS FIBERS

CROSS REFERENCE TO RELATED APPLICATIONS

This application is a continuation of U.S. patent application Ser. No. 13/569,905 filed on Aug. 8, 2012, titled "WOUND DRESSING OF CONTINUOUS FIBERS", which is a continuation of U.S. patent application Ser. No. 12/537,284 filed on Aug. 7, 2009, titled "WOUND DRESSING OF CONTINUOUS FIBERS", now abandoned, which claims the benefit of priority under 35 U.S.C. §119(e) to U.S. Provisional Application No. 61/147,179 filed on Jan. 26, 2009, titled "WOUND FILLER MATRIX WITH CONTINUOUS FIBER", U.S. Provisional Application Ser. No. 61/096,105 filed on Sep. 11, 2008, titled "WOUND CONTACT LAYER AND FILLER," and U.S. Provisional Application Ser. No. 61/188,370 filed on Aug. 8, 2008, titled "METHOD FOR TREATING A WOUND." The disclosures of all these prior applications are hereby incorporated herein by reference in their entireties and are to be considered a part of this specification.

BACKGROUND

1. Technical Field

The present disclosure relates generally to wound dressings, and in particular to a wound dressing including an assembly or tow of continuous long fibers for receiving and retaining wound fluids in the treatment of acute and chronic wounds.

2. Background of Related Art

Wound dressings are generally placed over a wound to protect and promote healing of the wound. In the case of exuding wounds, such as pressure sores, ulcers and burns, it is customary to provide a dressing having a packing or filler material for receiving, retaining or conveying the wound exudate as it is produced. Exudates may be conveyed from the wound bed, at least in part, due to wicking characteristics of the wound filler. Thus, the wound filler promotes healing by removing potentially harmful bacteria from the wound bed, and also prevents damage to the surrounding skin that can be caused by an excessively moist environment.

The dressing filler may capture the excess exudates for subsequent removal, e.g., when the dressing is replaced with a new dressing. Some materials, such as cotton, tend to shed fibers or fibrils (e.g., very short or irregular fibers jutting out from the main fiber structure) into the wound. These fibers may tend to remain in the wound when the dressing is changed. Removing these stray fibers can be a labor intensive procedure that may further damage the wound, and neglecting to remove these stray fibers may cause irritation and otherwise inhibit natural healing of the wound.

One technique that may utilize a dressing with an absorbent filler is known as negative wound pressure therapy (NWPT). The absorbent material may be positioned in a reservoir over the wound where a negative pressure may be maintained. The reservoir subjects the wound to a subatmospheric pressure to effectively draw wound fluid, including liquid exudates, from the wound without the continuous use of a vacuum pump. Hence, vacuum pressure may be applied once, or in varying intervals depending on the nature and severity of the wound. This technique has been found to promote blood flow to the area, stimulate the formation of granulation tissue and encourage the migration of healthy tissue over the wound. An NWPT apparatus may also serve to draw exudates from the absorbent material out of the dressing without requiring that the entire dressing be changed. When an NWPT procedure is complete, however, the absorbent material must be removed and is thus subject to the difficulties that may be caused by stray fibers. Accordingly, all absorbent filler suitable for use in wound dressings including those wound dressings adapted for use in advanced wound therapy procedures such as NWPT would be helpful.

SUMMARY

According to one aspect of the disclosure, a method for treating a wound includes using a wound dressing comprising a plurality of fibers, each fiber having a length of at least two (2) inches. The method entails incorporating the wound dressing into a wound to keep the sides of the wound apart, and removing the wound exudate.

According to another aspect of the disclosure, a wound dressing apparatus is configured to promote the healing of a wound, and may be used in conjunction with an NWPT system. The apparatus includes a wound cover for defining a reservoir over a wound in which a negative pressure may be maintained by forming a substantially fluid-tight seal around the wound, a vacuum source in fluid communication with the reservoir and suitable for providing an appropriate negative pressure to the reservoir to stimulate healing of the wound, and a packing structure positioned between the wound and the wound cover. The packing structure includes a core of filler material substantially surrounded by a sheath of contact material. The filler material is adapted for receiving wound fluids, and may be adapted for transporting wound fluids from the wound. The sheath of contact material is adapted for direct contact with the wound, and is permeable to wound fluids to permit passage of wound fluids through the core.

The packing structure may define an elongate tube, and may exhibit a plurality of longitudinally spaced separation features adapted for dividing the packing structure. A pod defined between adjacent separation features may assume a closed configuration such that the sheath of contact material extends along opposite lateral edges of the pod. The separation features include a perforated tear line extending laterally across the packing structure and may be spaced apart from adjacent separation features by a distance of from about 50% to about 300% of a width of the packing feature.

In some embodiments of the disclosure, the contact material may comprise a directionally-apertured film, and the filler material may comprise a polypropylene tow. The sheath may comprise upper and lower sheets of the directionally-apertured film having a seal around a periphery to encapsulate the filler between the upper and lower sheets, and each of the upper and lower sheets may be arranged such that a male side of the directionally-apertured film is oriented toward the interior of the packing structure to encourage exudate flow into the packing structure. Other non-adherent materials are also envisioned. Alternatively, one of the upper and lower sheets may be arranged such that a male side of the directionally-apertured film is oriented toward the interior of the packing structure, and the other of the upper and lower sheets may be arranged such that a mate side of the directionally-apertured film is oriented toward the exterior of the packing structure to encourage exudate flow through the packing structure. The packing structure may comprise upper and lower sheets of contact material having a seal around a periphery to encapsulate the filler material between the upper and lower sheets. Furthermore, the packing structure may comprise at least one interior seal to define a central pod that is encircled by at least one ring-shaped pod toward a circumferential region of the packing structure. A separation feature may be included on the seal. A plurality of progressively larger ring-shaped pods toward the circumferential region of the packing structure may be defined by a plurality of generally concentric interior seals.

The filler may include a foam layer adjacent one of the upper and lower sheets of contact material, and a tow layer adjacent the foam layer. A foam layer may be disposed on each side of the tow layer, and a hole may be formed in the foam layer to promote the flow of wound fluids through the packing structure.

According to another aspect of the disclosure, a wound dressing for use with wounds includes a core of filler material, and a sheath of contact material substantially surrounding the core. The core of filler material is adapted for receiving wound fluids, and may also be adapted for transporting wound fluids from the wound. The contact material is adapted for positioning in direct contact with the wound, and the sheath is permeable to permit passage of the wound fluids into and through the core. A plurality of longitudinally spaced separation features is adapted for dividing the wound dressing, and adjacent separation features define a pod there between. A plurality of pods may be arranged to define a two dimensional array. The contact material may comprise a directionally-apertured film, and the filler material may comprise a polypropylene tow.

According to still another aspect of the disclosure, a wound dressing for use with wounds includes a core of filler material comprising a polypropylene tow, a sheath of contact material substantially surrounding the core and comprising a directionally-apertured film, and a seal at a periphery of the sheath of contact material encapsulating the core within the sheath of contact material.

According to another aspect of the disclosure, a wound filler for use with a negative wound pressure therapy apparatus, e.g., may include a wound dressing for defining a reservoir over a wound in which a negative pressure may be maintained by forming a substantially fluid-tight seal around the wound, a vacuum source in fluid communication with the reservoir and being suitable for providing an appropriate negative pressure to the reservoir to help stimulate healing of the wound, and a wound filler matrix disposed within the wound dressing. The wound filler matrix defines a length along a longitudinal axis and comprises at least one continuous fiber configured in a plurality of loop segments traversing the longitudinal axis. The wound filler matrix further includes a connecting segment extending along the longitudinal axis and connected to at least some of the loop segments. The connecting segment may maintain the integrity of the at least one continuous fiber thereby facilitating placement and removal from the wound bed. The connecting segment may be connected to each loop segment. The connecting segment may be adapted to be severed to provide a segment of the wound filler matrix to accommodate wounds of various sizes and types. The connecting segment may be dimensioned to define a handle segment extending longitudinally beyond the at least one continuous fiber.

The connecting segment and the at least one continuous fiber may comprise different material. The at least one continuous fiber may include multifilaments. The at least one continuous fiber of the wound filler matrix may be non-absorbent, and may include an additive.

In another embodiment, a wound dressing apparatus includes a cover layer adapted to cover a wound to provide a microbial barrier over the wound and a wound filler matrix for 'receiving wound fluids. The wound filler matrix may include a continuous fiber arranged in a tow configured by passing a connecting segment through the fiber to gather the fiber into a plurality of loop segments.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 7A is a top plan view of an alternate embodiment of a packing structure;

FIG. 7B is a cross sectional view of the packing structure of FIG. 4A;

FIG. 7C is a perspective view of a male side of a directionally-apertured film;

FIGS. 10A-10C are cross sectional views of alternate embodiments of a packing structure;

FIG. 12A is a cross-sectional view of the wound filler matrix taken along the lines 12A-12A of FIG. 12;

FIG. 12B is a cross-sectional view similar to the view of FIG. 2A of an alternate embodiment of the wound filler matrix; and FIGS. 13A through 13I are partial orthogonal views depicting various configurations for a multifilament fiber of the wound filter matrix of the present disclosure.

DETAILED DESCRIPTION

Figure 1A:
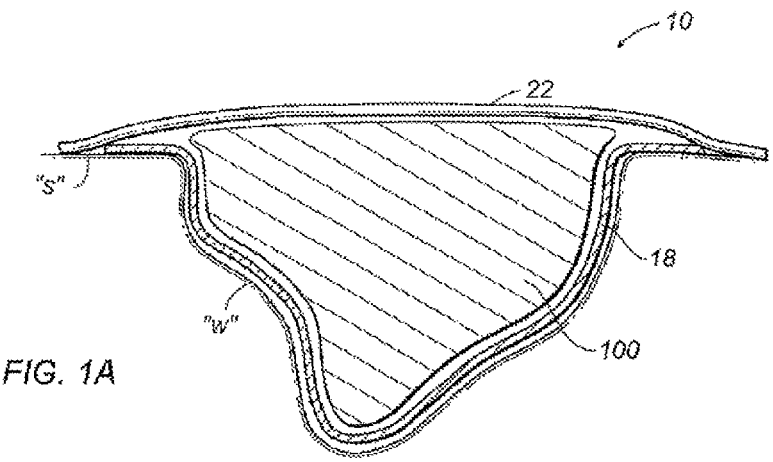
FIG. 1A is a cross sectional view of a wound dressing apparatus formed in accordance with the present disclosure.

The present disclosure relates to treatment of a wound using a wound dressing comprising a plurality of fibers, each fiber having a length of at least two (2) inches and in one embodiment, at least 4 inches and in other embodiments, at least 6 inches, and at least 8 inches. The method of treatment entails incorporating the wound dressing into a wound to keep the sides of the wound apart, and removing the wound exudate.

In more detail, the fiber of the wound dressing may be any fiber having a length of at least two (2) inches. Included within the suitable fibers are natural fibers and man-made fibers.

Examples of suitable fibers are natural fibers produced by plants, animals and/or geologic processes. For example, natural fibers include alginates, chitosan, rayon, vegetable fibers, which may be generated from arrangements of cellulose and bound together by lignin as in cotton, hemp, jute, flax, ramie and sisal, for example. Also, wood fibers are derived from tree sources and include groundwood, thermomechanical pulp (TMP) and bleached or unbleached kraft or sulfite (sulphite) pulps formed by a manufacturing process wherein lignin is removed to free the fibers from the wood structure. Animal fibers consist largely of proteins and include spider silk, sinew, catgut, wool and hair such as cashmere, mohair and angora, and chitosan for instance. There are also mineral sources for natural fibers such as woolastinite, attapulgite, halloysite, and asbestos.

Suitable man-made fibers include regenerated fibers and synthetic fibers. Regenerated fibers are those fabricated from natural materials by processing these materials to form a fiber structure. For example, regenerated fibers may be derived from the pure cellulose in cotton and wood pulp to form such products as rayon and cellulose acetates. Fibers may also be regenerated from mineral sources such as glass or quartz to form fiberglass or optical fibers. Ductile metals such as copper gold or silver may be drawn to form metallic fibers, and more brittle materials such as nickel aluminum or iron may be extruded or deposited.

Synthetic fibers are made entirely from synthetic materials such as petrochemicals, and are usually stronger than either natural or regenerated fibers. Synthetic fibers (as well as regenerated acetate fibers) tend to be thermoplastic, i.e., they are softened by heat. Therefore, these fibers may be shaped at high temperatures to add such features as pleats, creases and complex cross sections. Synthetic fibers may be formed from materials such as polyamide nylon, polyethylene terephthalatae (PET) or polybutylene teraphalate (PBT) polyester, phenol-formaldehyde (PF), polyvinyl alcohol (PVOH), polyvinyl chloride (PVC) and polyolefins such as polypropylene (PP) and polyethylene (PE).

The fibers of the wound dressing may be gathered. Gathering of the fibers may be achieved by any known manner. For example, gathering of fibers may be achieved by any one or more of the following methods. The fibers may be gathered by entangling the fibers; or intermingling the fibers; or wrapping the fibers with yarn; or thermally bonding the fibers; or ultrasonically treating the fibers; or radio frequency (RF) bonding; or adhering; or tying; or combinations of the methods; and the like.

Furthermore the fibers may be absorbent or non-absorbent with respect to the wound exudate.

The fibers may have a denier of about 3 to about 25 deniers per fiber, in one embodiment, and, in another embodiment, from about 3 to about 16 deniers per fiber.

The fibers may be crimped by any known technique such as, for example, by steam jet crimping, air jet crimping, stuffer box crimping, or self crimping.

The fibers may be treated to increase the properties of wicking and/or hydrophobicity, by any known technique. For example, the fibers may be treated with PHOBOL 7811 aqueous fluorochemical dispersion, available from Huntsman Chemicals. The dispersion may be applied to the fiber using a dip and squeeze padder or similar application method. The concentration of the dispersion can be adjusted by dilution with water to adjust the level of dispersion applied to the fibers. If desired, other suitable treatments include the use of hydrophobic aqueous binders such as AIRFLEX 140 available from Air Products, silicones, and a polyurethane such as RU41-773 available from Stahl.

It is also possible to improve the wicking and/or hydrophobicity properties of the fibers by using a melt additive such as HYD-REPEL, available from Goulston Technologies, which increases the water repellency property of the fibers. All of the fiber may be treated or a core/sheath fiber may be produced with the HYD-REPEL melt additive in the sheath.

The fibers herein may be lofted or opened to increase apparent density or volume, by any known technique. For example, one suitable method is described in U.S. Pat. No. 3,328,850. It is described therein that a material which in the present document, is a fiber, may be opened by passing the fiber to the nip of a pair of rolls, one of which has a smooth rubbery surface. The rolls are moving at a speed faster than the speed of the fibers, and the fibers leaving the nip are passed through an air-spreading zone, in which the fibers are confined between two parallel walls. The fibers are subjected to streams of air from the walls. This is only one suitable manner of lofting or opening the fibers. Any other means for lofting or opening the fibers may be utilized The fibers may be combined with, or treated with, any additive or agent that enhances the healing of the wound. For example, agents such as polyhexamethylene biguanide (PHMB), or any other medicaments, antimicrobials, wound healing agents, and/or wound debriding agents, may be used to decrease the incidence of infection or otherwise promote healing of the wound. Other agents include those used in slow release treatments wherein the agent is released from the fiber into the wound over a period of time.

The fibers may contain additional active ingredients or agents such as, for example, a therapeutic agent, an organoleptic agent and a pharmaceutical agent including, for example, an anti-microbial agent, in growth factor, an analgesic, a tissue scaffolding agent, a wound debriding agent, a hemostatic agent, an anti-thrombogenic agent, an anesthetic, an anti-inflammatory agent, an anticancer agent, a vasodilation substance, a wound healing agent, an angiogenic agent, an angiostatic agent, an immune boosting agent, a skin sealing agent, combinations thereof and the like.

Suitable anti-microbial agents that can be used include, but are not limited to, anti-microbial metal ions, a chlorhexidine, a chlorhexidine salt, a triclosan, a polymoxin, a tetracycline, an amino glycoside (e.g., gentamicin or Tobramycin™), a rifampicin, a bacitracin, an erythromycin, a neomycin, a chloramphenicol, a miconazole, a quinolone, a penicillin, a nonoxynol 9, a fusidic acid, a cephalosporin, a mupirocin, a metronidazole, a secropin, a protegrin, a bacteriolcin, a defensin, a nitrofurazone, a mafenide, an acyclovir, a vanocmycin, a clindamycin, a lincomycin, a sulfonamide, a norfloxacin; a pefloxacin, a nalidizic acid, an oxalic acid, an enoxacin acid, a ciprofloxacin, combinations thereof and the like. In certain embodiments, a preferred anti-microbial agent can include at least one of polyhexamethylene biguanide (PHMB), a PHMB derivative such as, for example, a biodegradable biguanide (e.g., polyethylene hexamethylene biguanide (PEHMB)), chlorhexidine gluconate, chlorhexidine hydrochloride, ethylenediaminetetraacetic acid (EDTA), variations of EDTA such as, for example, disodium EDTA or tetrasodium EDTA, combinations thereof and the like. In further exemplary embodiments, the antimicrobial agent can be PHMB.

The method for treating wounds using the fibers herein is comprised as follows.

(a) Providing a wound dressing comprising a plurality of fibers, each fiber having a length of at least two (2) inches, and in one embodiment, at least four (4) inches, and in other embodiments, at least 6 inches, and at least 8 inches;

(b) Incorporating into the wound to be treated an amount of the wound dressing that is sufficient to cause the walls of the wound to remain apart thereby allowing the wound to heal from the inside to the outside of the wound; and (c) Removing exudate from the wound.

In respect of the method herein for treating a wound, the fibers of the wound dressing may be absorbent or non-absorbent with respect to the wound exudate.

Moreover, as described herein, the fibers of the wound dressing may have a denier of about 3 to about 25 deniers per fiber; or may be treated to have increased volume; or may be treated to have increased wicking ability; or may be crimped; or may be lofted; or may be combined with, or treated with, an additive, such as PHMB, that reduces infection of the wound.

In the method herein, the wound dressing comprising the fibers herein, is incorporated into a wound in any amount that is sufficient to cause the walls of the wound to remain apart thereby allowing the wound to heal from the inside to the outside of the wound. In one embodiment, the amount of the wound dressing incorporated into the wound ranges from about 25% based on the volume of the wound to an amount of wound dressing that exceeds the volume of the wound. In another embodiment, the amount of the wound dressing incorporated into the wound ranges from about 50% to about 100% of the volume of the wound and in another embodiment, the wound dressing is incorporated into the wound in an amount equal to the wound volume.

In another embodiment, the wound dressing that is incorporated into the wound exerts pressure against the walls of the wound.

In the method herein, it is required that the wound exudate be removed from the wound. The wound exudate may be removed from the wound by any known technique. In one embodiment, where the fibers of the wound dressing are non-absorbent in respect of the wound exudate, the wound exudate may be removed by any type vacuum technique such as negative pressure wound therapy (NPWT). In another embodiment, where the fibers of the wound dressing are absorbent in respect of the wound exudate, the wound exudate may be removed by removing the wound dressing containing the absorbed wound exudate from the wound. In this instance, removal of the wound dressing containing the absorbed wound exudate, may be followed by incorporating a new wound dressing comprised of absorbent fibers, as needed.

In one embodiment, an example of a technique that may be utilized with a wound dressing comprising a non-absorbent fiber is known as negative pressure wound therapy (NPWT). The wound dressing comprising non-absorbent fibers may be positioned in a reservoir above a wound where a negative pressure may be maintained. The reservoir subjects the wound to a sub-atmospheric pressure to effectively draw wound fluid, including liquid wound exudate, from the wound without the continuous use of a vacuum pump. Vacuum pressure may be applied once, or in varying intervals, depending on the nature and severity of the wound.

Various crimping and bulking methods are contemplated to permit individual fibers or a plurality of fibers to separate in areas such that the fibers may receive and transport wound fluids. An air jet crimping process may be used wherein a fiber is directed past turbulent streams of compressed air to entangle the individual fibers into a multitude of loops and convolutions. A steam jet crimping process may also be used wherein a fiber is directed past turbulent streams of a high temperature steam to not only produce loops and convolutions, but also to heat set these same loops and convolutions. Another crimping process is known as stuffer box crimping. Stuffer box crimping is a process by which a fiber may be forcibly fed into a crimping chamber having a restricted exit. Subsequent portions of the fiber entering the crimping chamber will impart a force causing the fiber to buckle inside the chamber until, upon emergence from the chamber, the fiber retains a crimp therein. Any of these crimping processes may be used.

It is advantageous to utilize as the wound dressing a plurality of fibers with each fiber having a length of at least two (2) inches, in the method described herein for treating a wound. Individual fibers having a length of at least two (2) inches will have less tendency to separate from the rest of the fibers. This will minimize loose fibers that might remain in the wound, and which could cause inflammation or other impairments of the wound healing. The fibers having a length of at least two (2) inches can be gathered to further minimize the possibility of loose fibers remaining in the wound.

Furthermore, the fibers having a length of at least two (2) inches can be modified for example. by crimping or chemical treatment to provide optimum wound properties that are important to wound healing. These include wound exudate flow, wound exudate retention, conformance to wound, an antimicrobial properties.

Referring to FIG. 1, a wound dressing apparatus according to the present disclosure is depicted generally as 10 for use on a wound "w" surrounded by healthy skin "s." The apparatus 10 includes a contact layer 18 placed in contact with the wound "w," a wound dressing 100 placed into the wound "w" over the contact layer 18 and a cover layer 22 placed in contact with the skin "s" to cover the wound dressing 100 and wound "w."

Contact layer 18 may be formed from perforated film permitting exudates to be drawn through the contact layer 18 into the wound dressing 100. Passage of wound fluid through the contact layer 18 may be substantially unidirectional such that exudates do not tend to flow back into the wound "w." Unidirectional flow may be encouraged by directional apertures. such as cone-shaped formations protruding from the film material (see, e.g. FIG. 7). Arranging the contact layer 18 such that the formations protrude in the direction of the wound dressing 100 allows for exudates to encounter the film as an array of cone-shaped formations in the direction away from the wound "w" and as an array of collecting basins in the direction toward the wound "W." Unidirectional flow may also be encouraged by laminating the contact layer 18 with materials having absorption properties differing from those of contact layer 18. A non-adherent material may be selected such that contact layer 18 does not tend to cling to the wound "w" or surrounding tissue when it is removed. One material that may be used as a contact layer 18 is sold under the trademark XEROFORM® by Tyco Healthcare Group LP (d/b/a Covidien).

Wound Dressing 100 is positioned in the wound "w" over the contact layer 18 and is intended to receive and retain wound exudates. Wound dressing 100 is conformable such that it may assume the shape of any wound "w" and may be packed up to any level, e.g. up to the level of healthy skin "s" or to overfill the wound such that wound dressing 100 protrudes over the healthy skin "s."

As discussed in greater detail below, the wound dressing 100 may be formed from an assembly of fibers each of which fibers having a length of at least 2 inches.

Cover layer 22 may assume a variety of forms typically used to cover a wound "w" in wound care applications. For example, cover layer 22 may be formed from a flexible polymeric or elastomeric film having an adhesive coating on an underside to fasten the film to the surrounding skin "s." Thus cover layer 22 may serve as a microbial barrier to help prevent contaminants from entering the wound "w." In disclosed embodiments, cover layer 42 may be formed from a moisture vapor permeable membrane to promote the exchange of oxygen and moisture between the wound "w" and the atmosphere. A membrane that provides a sufficient moisture vapor transmission rate (MVTR) is a transparent membrane sold under the trade name POLYSKIN®II by Tyco Healthcare Group LP (d/b/a Covidien). A transparent membrane helps permit a visual assessment of wound conditions to be made without requiring removal of the cover layer 22. Alternatively, cover layer 22 may comprise an impermeable membrane 22.

Figure 1B:
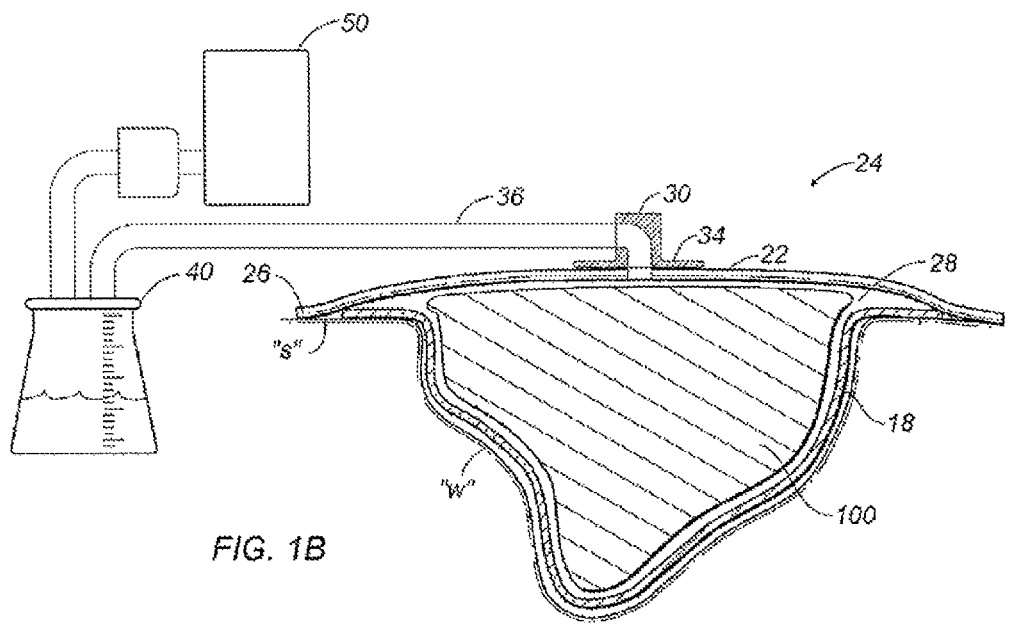
FIG. 1B is a cross sectional view of an alternate wound dressing apparatus formed in accordance with the present disclosure.

Referring now to FIG. 1B, the wound dressing 100 of the present disclosure may also be used in any wound dressing applications such as a negative pressure wound therapy (NPWT) apparatus 24. Such an apparatus 24 may include a wound dressing having a contact layer 18 and wound dressing 100, as described with reference to FIG. 1A. Cover layer 22 may be particularly adapted for such an application. For instance, cover layer 22 may include a substantially continuous band of a biocompatible adhesive at the periphery 26 such that the adhesive forms a substantially fluid-tight seal with the surrounding skin. Thus, cover layer 22 may act as both a microbial barrier to help prevent contaminants from entering the wound "w," and also a fluid barrier to help maintain the integrity of a vacuum reservoir 28.

A vacuum port 30 having a flange 34 may also be included to facilitate connection of the reservoir 28 to a vacuum system. The vacuum port 30 may be configured as a rigid or flexible, low-profile component, and may be adapted to receive a vacuum tube or fluid conduit 36 in a releasable and fluid-tight manner. An adhesive on the underside of flange 34 may provide a mechanism for affixing the vacuum port 30 to the cover layer 22, or alternatively flange 34 may be positioned within reservoir 28 (not shown) such that an adhesive on an upper side of the flange 34 affixes the vacuum port 30. However the vacuum port 30 is affixed to the cover layer 22, a hollow interior of the vacuum port 30 provides fluid communication between the fluid conduit 36 and the reservoir 28. Vacuum port 30 may be provided as a pre-affixed component of cover layer 22, as a component of fluid conduit 36 or entirely independently. Alternatively, vacuum port 30 may be eliminated if other provisions are made for providing fluid communication with the fluid conduit 36.

Fluid conduit 36 extends from the vacuum port 30 to provide fluid communication between the reservoir 28 and collection canister 40. Any suitable conduit may be used for fluid conduit 36 including those fabricated from flexible elastomeric or polymeric materials. Fluid conduit 36 may connect to the vacuum port 30, the canister 40, or other apparatus components by conventional air-tight means such as friction fit, bayonet coupling, or barbed connectors, for example. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown, or alternatively a flexible polymeric pouch may be appropriate. Collection canister 40 may contain an absorbent material to help consolidate or help contain the wound drainage or debris. For example, super absorbent polymers (SAP), silica gel, sodium polyacrylate, potassium polyacrylamide or related compounds may be provided within canister 40. At least a portion of canister 40 may be transparent or translucent to assist in evaluating the color, quality and/or quantity of wound exudates. A transparent or translucent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NPWT apparatus 24. Vacuum source 50 may comprise a peristaltic pump, a diaphragmatic pump or other mechanism that is biocompatible and draws fluids, e.g. atmospheric gasses and wound exudates, from the reservoir 28 appropriate to help stimulate healing of the wound "w." In disclosed embodiments, the vacuum source 40 is adapted to produce a sub-atmospheric pressure in the reservoir 28 ranging between about 20 mmHg and about 500 mmHg, more specifically, between about 75 mmHg to about 125 mmHg. One suitable peristaltic pump is the Kangaroo PET Eternal Feeding Pump manufactured by Tyco Healthcare Group LP (d/b/a Covidien).

Figure 2A:
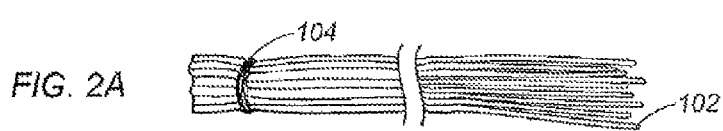
FIGS. 2A through 2I are partial orthogonal views depicting various configurations for a wound filler as depicted in FIGS. 1A and 1B.
Figure 2B:
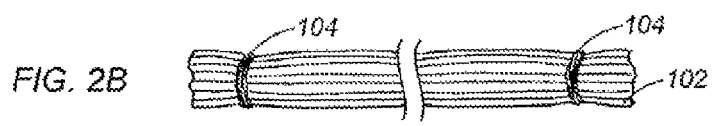
Figure 2C:
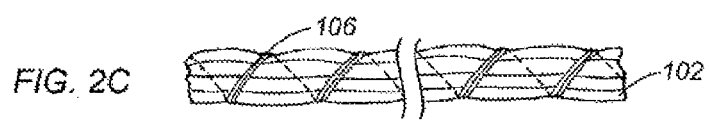
Figure 2D:
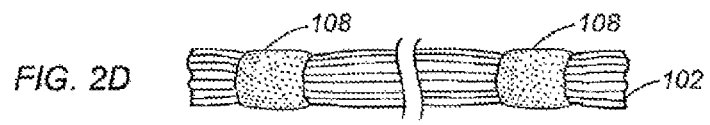

Referring now to FIG. 2A, the wound dressing 100 of the present disclosure may generally assume the form of a bundle, assembly or tow of fibers each of which fibers having a length of at least 2 inches. The fibers 102 may be arranged 50 as to be generally non-intersecting along their length. Although not necessarily parallel, the fibers 102 may be generally free from entanglement or interlacing. At least one gathering feature 104 may be included to permit the bundle to help resist separation of fibers 102. A single gathering feature 104 may be formed from a separate fiber wrapped or tied around the bundle to compress the bundle in a localized region. Alternatively, gathering features 104 may be placed intermittently along the bundle, as shown in FIG. 2B, to help secure the tow at multiple locations, or separate fibers may be wrapped helically around the bundle as in FIG. 2C to form gathering feature 106.

Figure 2E:
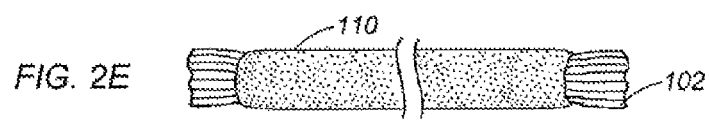
Figure 2F:
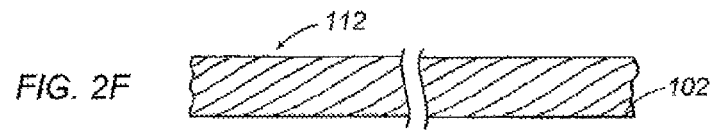

A tow may be enclosed with a self-sealing, non-woven mesh or other porous sheet to form gathering feature 108. A self-sealing gathering feature 108 may be an elastic or slightly undersized band such that fibers 102 may be inserted through an open end of the band to be constrained under compression. Alternatively, gathering features 108 may include an adhesive component such that a flat strip may be wrapped around the tow and the flat strip may be affixed by adhering either to itself or to the fibers 102 with the adhesive component. As depicted in FIG. 2E, a gathering feature 110 may be formed with a substantial length of a non-woven mesh or a porous sheet to enclose a substantial length of the tow.

Figure 2G:
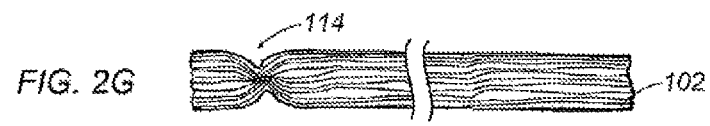
Figure 2H:
Figure 2I:

As depicted in FIGS. 2F through 2I the fibers 102 may be arranged or constructed as shown to help permit the tow to resist separation of fibers 102. Fibers 102 may be twisted as in a rope to provide a gathering feature 112 (FIG. 2F), or fibers 102 may be entangled by various processes to form a gathering feature 114 (FIG. 2G). Jets of steam, air or water may be directed at localized regions in the tow to entangle fibers 102 and provide gathering feature 114. Another entangling process involves needles used in a manner similar to needle punching to entangle fibers 102. A gathering feature 116 (FIG. 2H) may be provided simply by bonding fibers 102 with an adhesive, or by incorporating a binding material having a lower melting temperature than the fibers 102. By heating the tow, the binding material may melt and bind the fibers together upon cooling. A binding material may be provided along with one or more of the individual fibers in a co-extrusion such as a core-sheath arrangement, as described in greater detail below. As depicted in FIG. 2I, a gathering feature 118 may also be provided by crimping fibers to provide some degree of entanglement, as described in greater detail below. It is also envisioned that the arrangement of fibers 102 may include two or more of the features shown in FIGS. 2A through 2I.

Figure 3A:
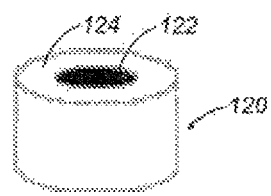
FIGS. 3A through 3G are schematic views depicting various co-extrusion arrangements for individual fibers as depicted in FIGS. 2A through 2I.
Figure 3B:
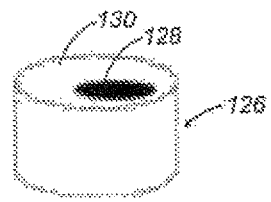
Figure 3C:
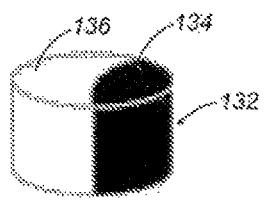

Referring to FIGS. 3A through 3G, two or more distinct polymers may be co-extruded to generate a fiber with specialized characteristics. For example, a fiber 120 exhibiting a concentric sheath-core arrangement is depicted in FIG. 3A. A core polymer 122 is surrounded by a sheath polymer 124. As discussed above, sheath polymer 124 may exhibit a lower melting temperature than core polymer 122 such that the sheath polymer 124 may be melted to provide a binder for fibers 102. Other applications for a sheath-core arrangement may include providing a high strength structural core polymer 122 and a sheath polymer 24 with surface characteristics appropriate to help promote wicking of wound fluid or to accept any of the beneficial polymer additives discussed below. A fiber 126 exhibiting an eccentric sheath-core arrangement is depicted in FIG. 3B including an off-center core polymer 128 and corresponding sheath polymer 130. This arrangement may be used to provide a self-crimping fiber 126 when the core polymer 128 and sheath polymer 130 are provided with differing shrinkage characteristics when subject to a temperature change. When heated, the fibers 126 may curl into a helix that is retained when the fiber is cooled, thus developing a crimp or bulk in an otherwise flat fiber 126. Such a self-crimping procedure may be further facilitated by using a side-by-side arrangement as depicted in FIG. 3C. Fiber 132 is similar to fiber 126, but differs in that core polymer 134 and sheath polymer 136 each occupy a portion of the outer surface of the fiber 132. With a proper polymer selection, the side-by-side arrangement of fiber 132 may yield higher levels of latent crimp than the eccentric sheath-core arrangement of fiber 126.

Figure 3D:
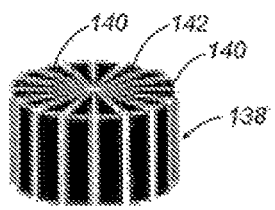
Figure 3E:
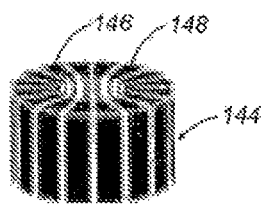

As shown in FIG. 3D, a fiber 138 having a pie-wedge arrangement may include alternating wedges comprising polymers 140 and 142. The wedges may be split into the component wedges upon mechanical agitation. This may assist in forming a gathering feature 114 as discussed above with reference to FIG. 2O. The component wedges may yield localized areas of microfibers to assist in entangling the fiber 138. A fiber 144 exhibiting a hollow pie wedge arrangement including a hollow center core is depicted in FIG. 3E. Fiber 144 may require less agitation to split into component polymers 146, 148.

Figure 3F:
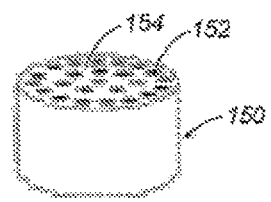

With reference to FIG. 3F, fiber 150 exhibits an islands-in-the-sea arrangement where one or more "island" polymers 152 are surrounded by a soluble "sea" polymer 154. This arrangement may provide for very fine strands of island polymers 152 to be effectively handled by manufacturing equipment. Once the island polymers 152 are in place, the soluble sea polymer is dissolved away. As many as about 37 or more island polymers 152 having a denier of about 0.04 (roughly 2 microns in diameter) may thus be handled effectively as a single fiber 150.

Figure 3G:
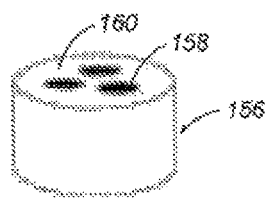

A fiber 156 exhibits a "three island" arrangement, as depicted in FIG. 3G. This arrangement includes three island polymers 158 surrounded by a sea polymer 160. Fiber 156 may be used in a manner similar to fiber 150 exhibiting an islands-in-the-sea arrangement, but may be more commonly used in a manner similar to fibers 120, 126 and 132 described above exhibiting a sheath-core arrangement. Fiber 156 may be described as including three core polymers 158 collectively having an increased surface area to discourage de-lamination from a potentially incompatible sheath polymer 160.

Figure 4A:
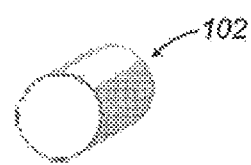
FIGS. 4A through 4F are schematic views depicting various cross sections of the individual fibers of FIGS. 2A through 2I.
Figure 4B:
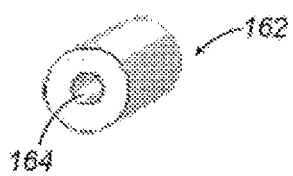

Referring to FIGS. 4A through 4F, individual fibers 102 may exhibit various cross sections to enhance a wicking capability or another characteristic of wound filler 100. A solid round cross section as depicted in FIG. 4A may be a standard for most synthetic fibers due to a relatively low cost when compared to another modified cross sections below. A fiber 162 is depicted in FIG. 4B having a void 164 in its cross section. Void 164 runs the entire length of the fiber 162 yielding a reduced density and rigidity of fiber 162 and permitting air to be trapped within. Such a cross section may facilitate crimping, entangling and/or lofting processes.

Figure 4C:
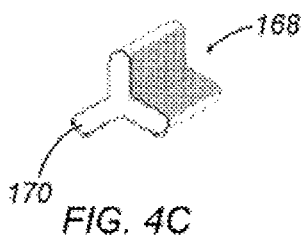
Figure 4D:

A multi-lobal cross section may also be used as depicted in FIG. 4C. Tri-lobal fiber 168 exhibits three arms 170 projecting from a central region offering rigidity and resilience to the wound dressing 100. A ribbon cross section as exhibited by fiber 174 depicted in FIG. 4D may be described as exhibiting a bi-lobal arrangement. A ribbon cross section offers a bending direction and shape well suited for segmented fibers which may be split into micro-fibers as described above with reference to FIGS. 3D and 3E. Such a cross section may be split into micro-fiber components with relatively minor agitation when compared to other cross sections.

Figure 4E:
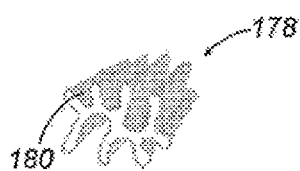

Highly modified cross section fibers 178 as depicted in FIG. 4E are sold under the trade name 4DG™ by Fiber Innovation Technology, Inc. Deep channels 180 of various sizes and configurations are provided along a longitudinal axis of the fiber 178 to help promote capillary wicking with its relatively large surface area. Fibers 172 having a 4DG™ cross section have demonstrated a capability to transport up to 2 liters of water per hour per gram of fiber.

Figure 4F:

A fiber 184 having a bowtie cross section as depicted in FIG. 4F may be well suited for use in a self-crimping fiber as described above with reference to FIG. 3B and FIG. 3C. Polymers with differing thermal characteristics may be arranged such that the centers of mass of the two polymers are separated by a relatively greater distance than other cross sections. A fiber 184 thus arranged may exhibit enhanced stretch recovery of the helical coils foamed by heating and subsequently cooling the fiber 184.

Self crimping may be accomplished with an eccentric core-sheath arrangement of polymers described above with reference to FIG. 3B or a side-by-side arrangement as described with reference to FIG. 3C. Another option to produce a self crimping tow is to combine full fibers of differing thermal characteristics in a creeling process. The crimped tow may be opened, i.e., the crimped fibers may be separated or spaced, to produce a particular texture or bulk. The crimped tow may be opened by air jets, or by longitudinal stretching and relaxing of the tow with a threaded roll assembly.

Figure 5:
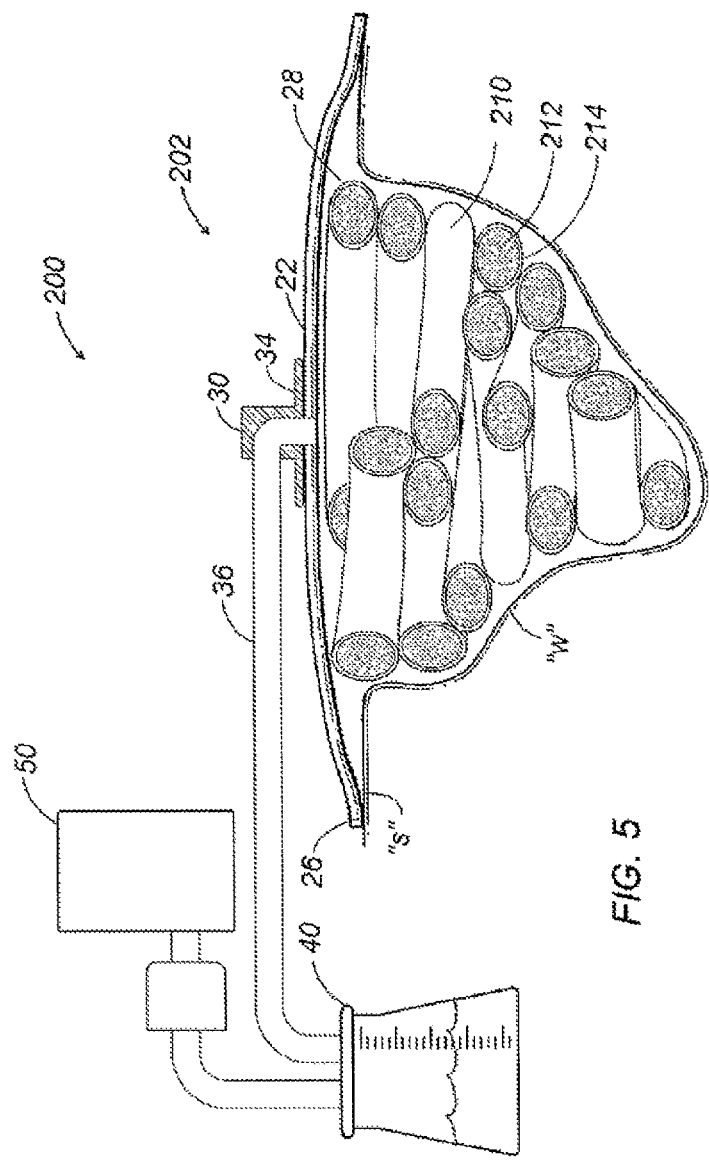
FIG. 5 is a cross sectional view of a wound dressing apparatus including a packing structure formed in accordance with another aspect of the present disclosure.

Referring now to FIG. 5, a negative wound pressure therapy apparatus according to the present disclosure is depicted generally as 200. Apparatus 200 includes a wound dressing assembly 202 defining reservoir 28 in fluid communication with vacuum source 50 as described above with reference to FIG. 1B. Wound dressing assembly 202 includes an elongate wound packing structure 210 comprising a core 212 substantially surrounded by a sheath 214. The core 212 may be formed from a dressing or filler material adapted for receiving and/or transporting wound exudates, and may include any material or structure described above with reference to FIG. 1A for use with wound dressing 100. The sheath 214 may be formed from a contact material 214 adapted for positioning in contact with the wound "w," and may include any material or structure described above with reference to FIG. 1A for use with contact layer 18. The sheath 214 is permeable to permit passage of wound fluids into and out of the core 212 of filler material. The packing structure 210 may be embodied as an elongate tube arranged to follow a winding path to substantially fill the wound "w" and conform to the particular geometry of the wound "w." Such an elongate tube may be provided in continuous lengths that may be conveniently cut at the time wound dressing assembly 202 is applied to accommodate the particular size of the wound "w." Such an arrangement may not require separate and independent sizing and subsequent application of a wound contact layer 18 and wound dressing 100.

Figure 6A:
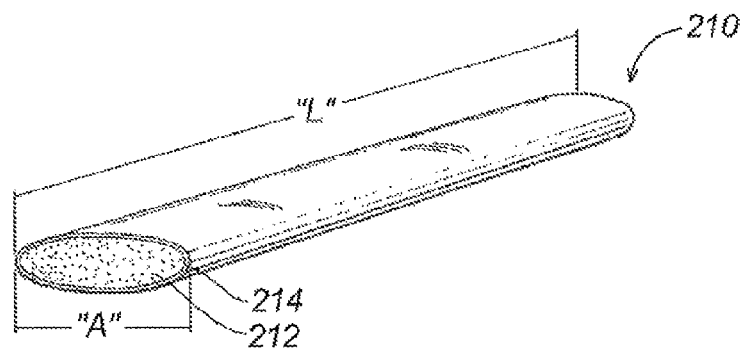
FIGS. 6A through 6C are partial perspective views depicting various configurations for the packing structure of FIG. 5.
Figure 6B:
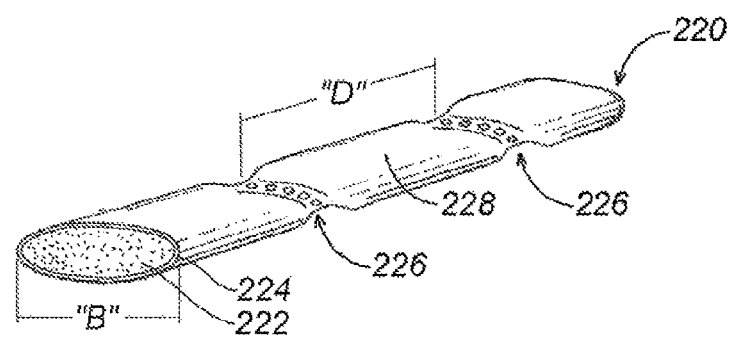
Figure 6C:
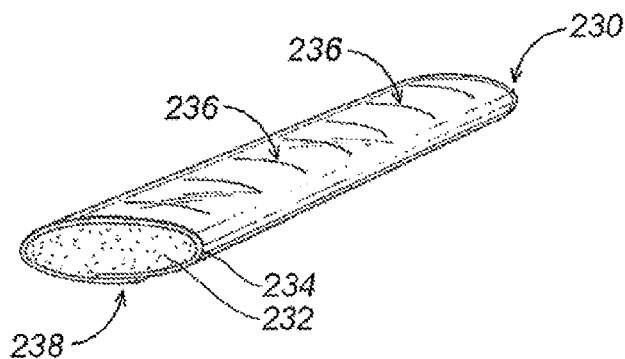

Referring now to FIGS. 6A through 6C, various configurations contemplated for a packing structure for use in NWPT apparatus 200 (FIG. 5) are depicted. As depicted in FIG. 6A, packing structure 210 defines an elongate tube having a length "L" extending in a longitudinal direction and a maximum width "A" extending in a lateral direction. The oblong cross section of packing structure 210 is substantially consistent along the length "L" of the packing structure 210. Other cross sections may be appropriate such as a round, hexagonal or other polygonal shapes. The sheath 214 may be formed by an extrusion or similar process providing for a seamless circumference around the core 212.

Packing structure 220, depicted in FIG. 6B, includes a core of filler material 222 substantially surrounded by a sheath of contact material 224. A plurality of longitudinally spaced separation features 226 provide for dividing the packing structure 220. A separation feature 226 may comprise a perforated tear line extending laterally across packing structure 220, which a clinician may use to cut or tear away a portion of the packing structure 220 such that packing structure 220 has an appropriate length to fill a wound "w" of a particular size. Separation features 226 may be spaced apart, for example, by a distance "D" of from about 50 percent to about 300 percent of a width "B" of the packing feature 220.

A series of pods 228 may be defined between adjacent separation features 226. Each pod 228 may have an open configuration wherein the core of filler material 222 extends between adjacent pods through the separation features 226. A portion of the dressing material 222 may thus be exposed across a lateral edge of the packing structure 220 when an adjacent pod 226 is removed. Alternatively, each pod 228 may have a closed configuration wherein the core of filler material 222 is interrupted in the vicinity of the separation feature 226. For example, the sheath of contact material 224 may be sealed to itself on the interior of packing structure 220 in the vicinity of the separation feature 226, such that the sheath of contact material 224 extends along opposite lateral edges of the pods 228. Such an arrangement of closed pods 228 may provide an area of increased flexibility in the vicinity of the separation feature 226 when compared to a central region of the pods 228. An area of increased flexibility may facilitate placement of packing structure 220 in a winding arrangement within the wound "w."

Referring now to FIG. 6C, packing structure 230 includes a core of filler material 232 substantially surrounded by a sheath of contact material 234. A separation feature 236 may comprise a slit or series of longitudinally spaced slits extending laterally across packing structure 230. Slits 236 may extend partially into the filler 232 such that the packing structure 230 is less resistant to cutting or tearing in the vicinity of the slits 236. The sheath of contact material 234 may be arranged with an overlap 238. Overlap 238 may facilitate application of a longitudinal adhesive bond, ultrasonic weld or similar seal to facilitate assembly of packing structure 230.

Referring now to FIG. 7A and FIG. 7B, packing structure 240 includes a core of filler material 242 substantially surrounded by a sheath of contact material 244. The sheath of contact material 244 includes upper and lower sheets 244U and 244L of contact material with a heat seal 246 formed around the periphery of the sheath 244 to encapsulate the filler 242 therein. An adhesive bond, ultrasonic weld; or similar seal may be incorporated as an alternative or in combination with heat seal 246 to encapsulate the filler 242. Packing structure 240 is a generally round, saucer or puck shaped capsule, but may alternatively be formed into a variety of shapes including spheres, cylinders, cubes, tetrahedrons and other polygonal shapes.

Filler 242 assumes the form of a polypropylene tow. A tow may be described as a loose, essentially untwisted strand of a large number of unidirectional synthetic fibers. Continuous filament polypropylene fibers may be arranged to form a loosely entangled ball to form a filler 142 capable of receiving wound exudates. The tow may be crimped, bulked or lofted to influence the absorptive, wicking or comfort characteristics of the filler 142. Various such processes and arrangements for the tow of filler 242 are described above with reference to FIGS. 2A through 4F.

Sheath 244 is formed from a non-adherent, directionally-apertured polyolefin film such as those manufactured by Tredegar Film Products, Corp. of Richmond, Va. These films are safe for contact with a wound "w" and permit fluid to flow into the filler 242. Unidirectional flow is encouraged through such a film by apertures formed at the peak of cone-shaped formations in the film material that project in one direction. Such a film will thus have a male side, as depicted in FIG. 7C, and an opposite female side. Fluid flow is encouraged across the film from the female side to the male side and discouraged in the opposite direction. Sheath 244 may be arranged such that the male side of such a film faces the interior of packing structure 240 from all directions. Fluid is thus encouraged to flow into the filler 242 regardless of the orientation in which the packing structure 240 is placed in the wound "w." Alternatively, the lower sheet 244L of sheath 244 may be oriented such that the male side faces the interior of the packing structure 240; while the upper sheet 244U of sheath 244 is oriented such that the male side faces the exterior of the packing structure 240. This arrangement encourages unidirectional flow through the entire packing structure 240. By placing packing structure 240 into the wound "w" with an orientation such that the lower sheet 244L in contact with the wound "w," wound fluids may be encouraged to flow into packing structure 240 by the directional apertures in the lower sheet 244L, and subsequently wicked through filler 242 to the upper sheet 244U where the directional apertures encourage flow out of the packing structure 240. Wound fluids may then be removed from wound dressing assembly 202 by vacuum source 50 and deposited in canister 40 (FIG. 5). Regardless of the orientation of upper and lower sheets 244U and 244L, sheath 244 should be pliable and soft when heat sealed such that packing structure 240 does not cause pain to the patient when placed inside a wound "w."

Figure 8A:
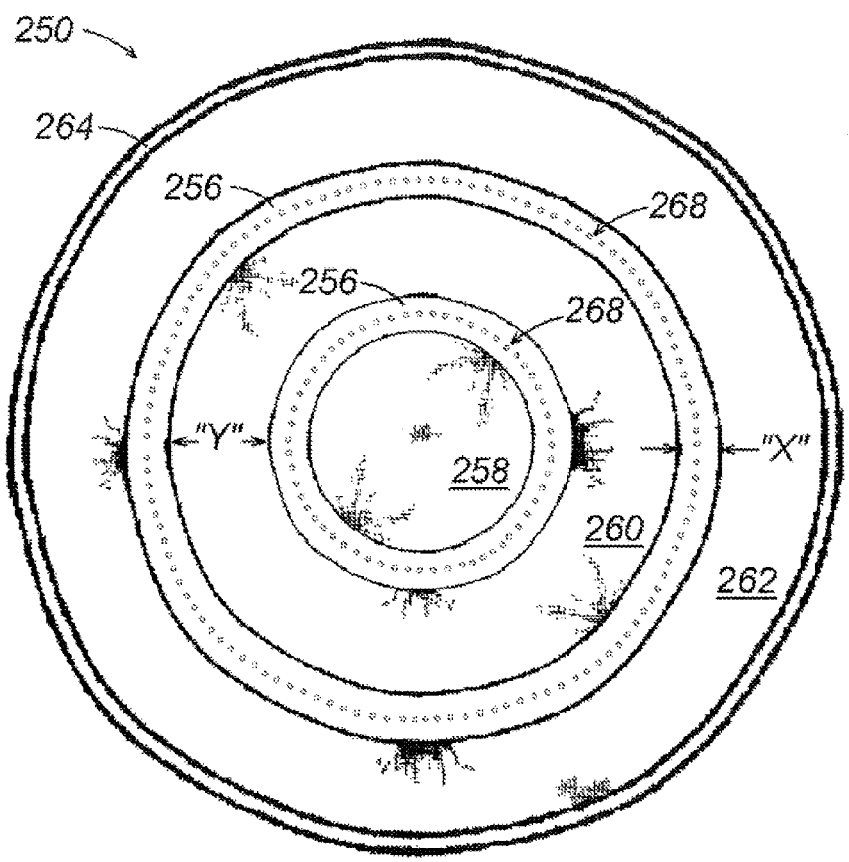
FIG. 8A is a top plan view of another alternate embodiment of a packing structure.
Figure 8B:
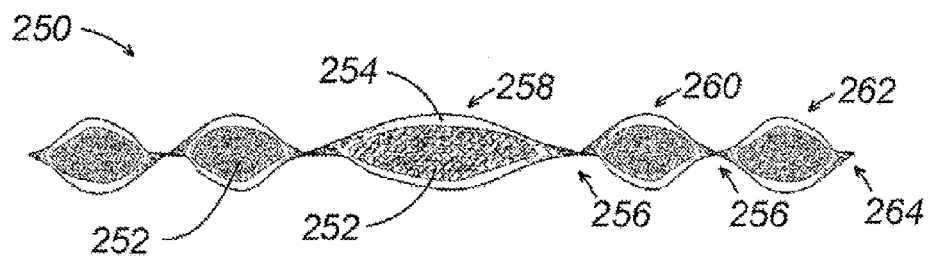
FIG. 8B is a cross sectional view of the packing structure of FIG. 5A.

Referring now to FIG. 8A and FIG. 8B, packing structure 250 includes a core of filler material 252 substantially surrounded by a sheath of contact material 254. A plurality of ring-shaped interior heat seals 256 are formed in a generally concentric arrangement between discrete segments of the filler material 252, thus dividing the packing structure 250 into a number of pods. A central pod 258 lies in the center of the packing structure 250, and is encircled by progressively larger ring-shaped pods 260, 262 toward the circumferential regions of the packing structure 250. An exterior heat seat 264 is formed around the periphery of packing structure 250 to close the outermost pod 262. A perforated ring 268 is formed on each of the interior heat seals 256 to provide a separation feature for the pods.

Although packing structure 250 is depicted as including only three distinct pods 258, 260 and 262, any number of pods may be formed into such an arrangement to form a packing structure of any desired size. Heat seals 256, 264 may have a width "X" of about 1 cm or less, and may be separated by a distance "Y" of about 1 inch to about 2 inches. In use, when the size of a particular wound "w" is assessed, outer pods, e.g. 262, may be removed using perforated ring 268 to permit packing structure 250 to assume an appropriate size for the wound "w."

Figure 9A:
FIGS. 9A-9F are cross sectional schematic views illustrating a manufacturing process used for the assembly of another alternate embodiment of a packing structure.

To manufacture a structure such as packing structure 240 and 250, a mold "m" may be formed as depicted schematically (in cross-section) in FIG. 9A. The mold "m" may include indentations "i" on an upper surface thereof, which are sized and spaced appropriately to form a desired number of pods. The mold depicted in FIG. 9A may be used to form a packing structure with four distinct pods including a central pod and three surrounding ring shaped pods.

Figure 9B:
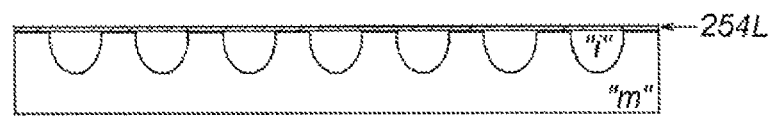
Figure 9C:
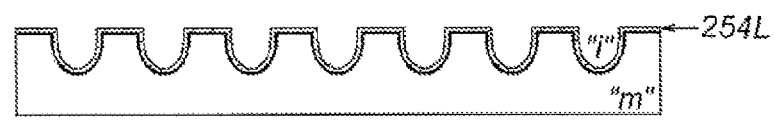
Figure 9D:
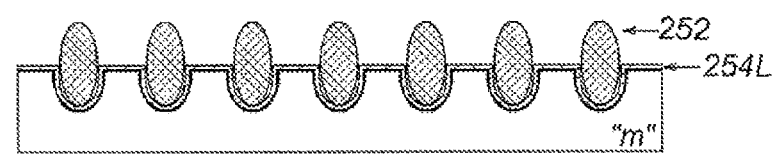

A flat sheet of sheath material 254L may be placed over the mold "m" (FIG. 9B) with a male side facing up. A directionally-apertured film such as those manufactured by Tredegar Film Products may be provided with, or marked with a distinguishing color on each side such that a proper orientation of the sheet may be verified. The sheet of sheath material 254L may then be drawn into the indentations "i" (FIG. 9C). Airflow may be directed through the mold "m" to draw in the sheath material 254L, or the sheath material 254L may be urged into place by any other suitable means.

Next, the filler material 252 may be positioned in the indentations "i" over the sheath material 254L, and may be arranged to overfill the indentations as depicted in FIG. 9O. A central indentation "i" may accommodate an entangled mass of polypropylene tow while surrounding indentations "i" may be conveniently filled by a twisted or spun rope of the tow material arranged in a circular fashion.

Figure 9E:
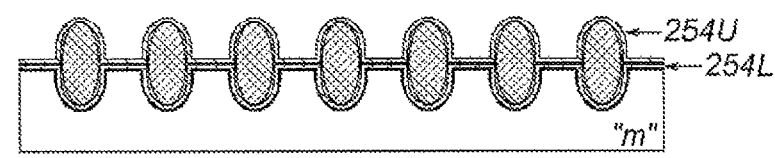
Figure 9F:
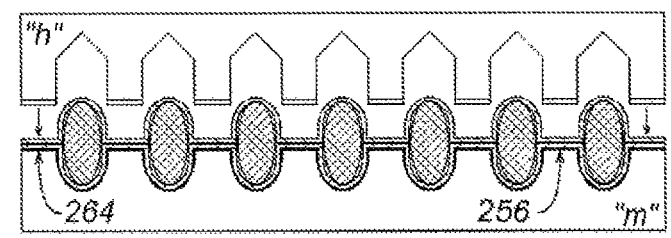

Another sheet of the sheath material 254U may be placed over the filler 252, and may be drawn downward into the intermediate spaces between the indentations in the mold "m" (FIG. 9E). The male side of the upper sheet of sheath material 254U may face downward toward the filler, and toward the male side of the lower sheet of sheath material 254L. An appropriate heat sealer "h" (FIG. 9F) having appropriately sized heat sealing rings may then be pressed down into each of the intermediate spaces to form interior heat seals 256, and another heat sealing ring may similarly form exterior heat seal 264. The heat sealing rings may include a Teflon® or similar coating such that the sheath material 254U does not tend to stick to the heat sealing rings. The heat sealing rings may alternately be applied individually, or the heat seals 256, 264 may be replaced by seals formed with a laser or ultrasonic welding mechanism that traverses a path around the filler 252 to encapsulate the filler 252.

Once the filler 252 has been encapsulated, the filler and the sheath material may be removed from the mold "m" for further processing. For example, the structure may be delivered to another apparatus for forming perforated rings 268 to complete the packing structure. Alternatively, the mold "m" or the heat sealer "h" may include a perforating mechanism (not shown) to form perforated rings 268 along with the formation of the heat seals 256, 264.

A variety of other embodiments of a packing structure may be formed with minor variations to the process described above. For example, the filler 252 may not necessarily overfill the indentations "i," but may be fill the indentations "i" up to the level of the top surface of the mold "m." Also, the upper layer of sheath material 254U may be replaced with a material that is dissimilar to the lower layer of sheath material. For example, the lower layer of sheath material 254L may be formed of a directionally-apertured polyolefin film while the upper layer may be formed of a porous or nonporous sheet of a polypropylene.

Figure 10C:
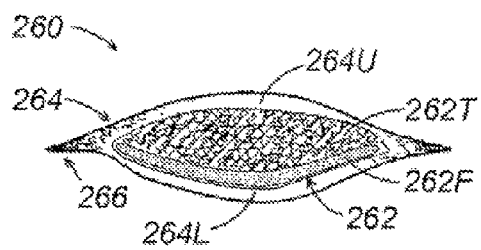
Figure 10C:
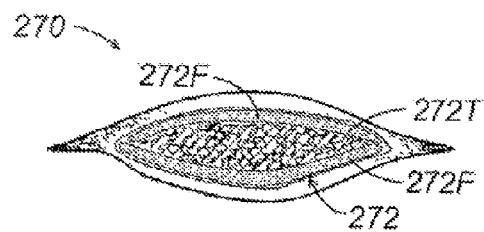
Figure 10C:
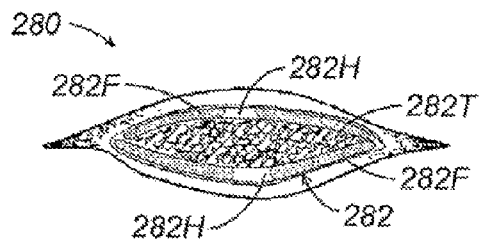

Referring now to FIG. 10A, packing structure 260 includes a core of filler material 262 substantially surrounded by a sheath of contact material 264. Similarly to sheath 244 discussed above with reference to FIG. 7B, the sheath of contact material 264 includes upper and lower sheets 264U and 264L of contact material with a seal 246 formed around the periphery to encapsulate the filler 262 therein. The upper and lower sheets 264U and 264L may be formed from a directionally-apertured film and may be oriented as discussed above. Filler 262 may be distinguished in that filler 262 is formed from at least two distinct materials.

Filler 262 comprises a layer of polypropylene tow is designated 262T, and a layer foam is designated 262F. Tow layer 262T may take any form discussed above with reference to FIG. 7A, and foam layer 262F may be formed from a resilient, open-cell foam such as polyurethane, polyester or polyolefin foam. Foam layer 262F may be effective to receive wound fluids from the wound, and may also readily release the wound fluids such that they may be removed from a dressing assembly 202 by a vacuum source 50 (see FIG. 5). Foam layer 262F exhibits uniform compression when subject to the evacuation cycles of an NWPT treatment such that potentially painful pressure points in the packing structure 260 are managed and the periphery of the wound "w" may be drawn inward evenly. The foam layer 262F may be positioned adjacent the lower sheet 264L of sheath 264 as depicted in FIG. 10A to provide a cushion to the wound bed. Alternative structures include a packing structure 270, which may include a filler 272 having a foam layer 272F on each side of a tow layer 272T. Packing structure 280, also includes a filler 282 having a foam layer 282 on each side of a tow layer 282T. A hole 282H is formed in each foam layer 282 to promote the flow of exudates through the packing structure 280.

Figure 11:
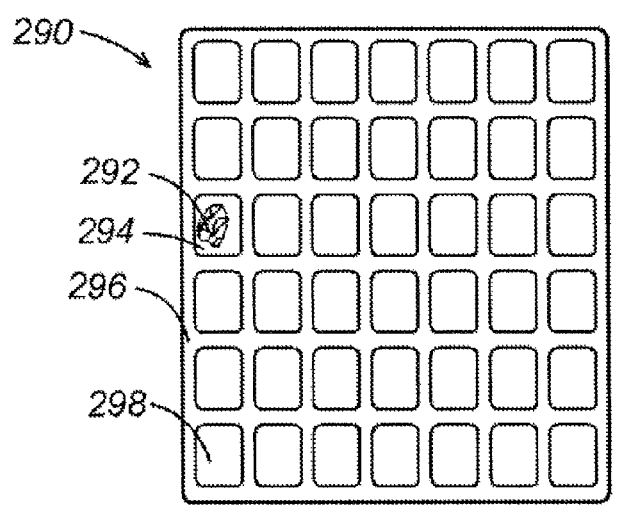
FIG. 11 is a top plan view of alternate embodiment of a packing structure.

Referring now to FIG. 11, packing structure 290 includes a core of filler material 292 substantially surrounded by sheath of contact material 294. A seal 296 is formed in the sheath of contact material 294 such that a plurality of pods 298 are formed in a two dimensional array. Pods 298 may vary in size, but are preferably about 1.25 inches in length by about 1.25 inches in width or smaller to provide a customizable packing structure 290. Depending on the particular dimensions of a wound "w" unnecessary pods 298 may be cut away to accommodate smaller wounds "w," or pods 298 may be folded onto one another along the seal 296 to accommodate deeper wounds "w." Perforations (not shown) may be formed in the sheath 294 along the seal 296 to provide a separation feature to facilitate removal of unnecessary pods 298. Alternatively, sheath 294 may be free of perforations to increase the strength and integrity of packing structure 290 inside a wound "w." A separation feature may thus be provided by creating a seal 296 wide enough to be readily cut by a clinician without inadvertently cutting into the core of filler 292. A packing structure 290 without perforations helps to insure individual pods 298 do not inadvertently become detached from the packing structure 290, and thus decreases the probability that a pod 290 will be inadvertently left in the wound "w."

Figure 12:
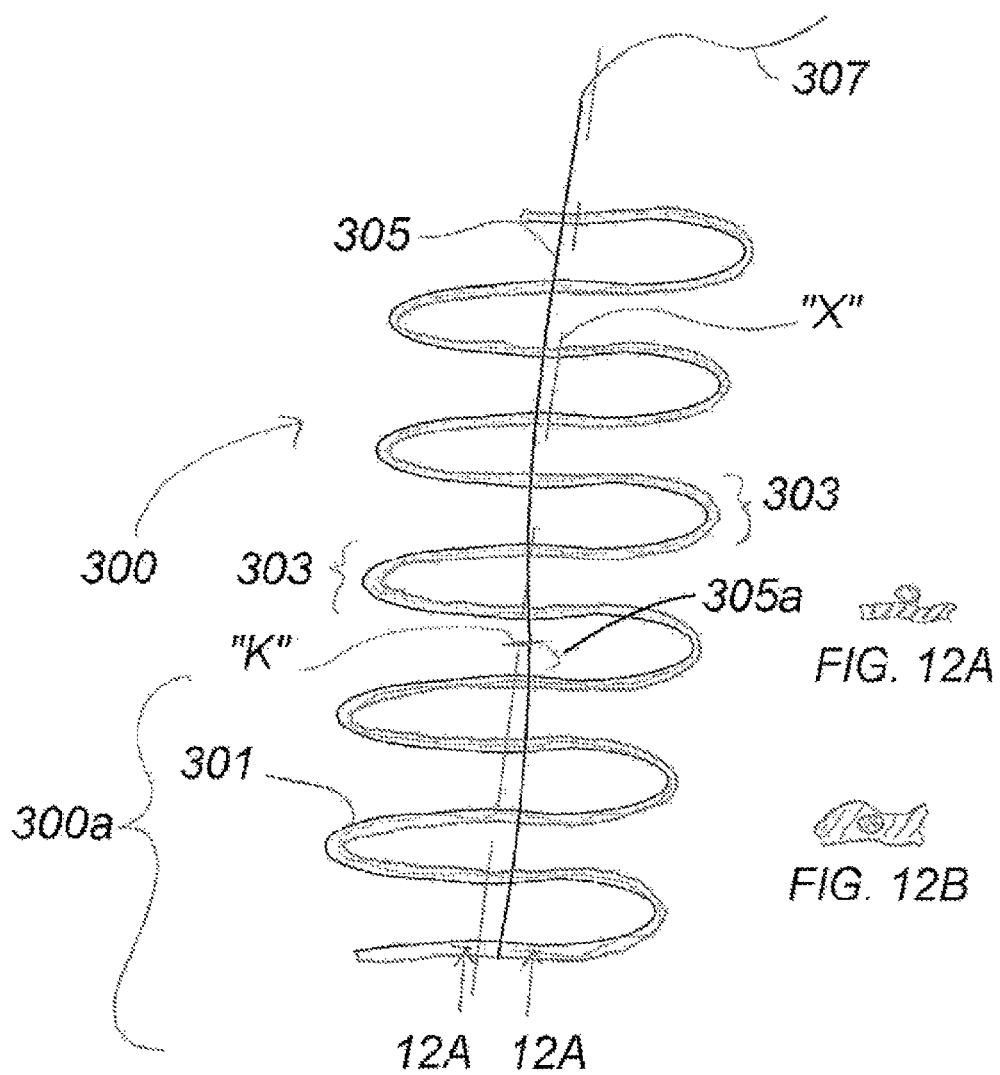
FIG. 12 is a schematic view depicting an embodiment of a wound filler matrix of the present disclosure.

According to another aspect of the disclosure, a wound filler matrix 300 of the present disclosure as depicted in FIG. 12 incorporates at least one continuous fiber comprising either natural or man-made filaments to form a structure suitable for conveying, transferring, and/or absorbing exudates. As indicated above, continuous filaments include those relatively long strands of a synthetic material such as nylon, rayon, etc., which may offer a smooth continuous outer surface substantially free of the protruding fibrils commonly associated with natural materials such as cotton. Because of the relatively smooth surfaces, structures such as fabrics or yarns formed from continuous filaments have a substantially lower tendency to become attached to a healing wound bed than do structures formed from natural filaments. Also, because of the relatively long length, continuous filaments have a substantially lower tendency to become separated from a structure and be inadvertently deposited in a wound as the dressing is changed.

The wound filler matrix 300 of the present disclosure may generally assume the form of a bundle, assembly, or tow of a continuous fiber. As illustrated in FIG. 12, the wound filler matrix 300 defines a length along longitudinal axis "x" about which at least one fiber 301 is disposed. Fiber 301 may be configured in a plurality of loop segments 303 which are arranged to traverse longitudinal axis "x." A connecting segment 305 extends along longitudinal axis "x" and is connected to at least several, possibly, all of the loop segments 303. Connecting segment 305 may be parallel or coincident to longitudinal axis "x". Connecting segment 305 may be stitched, pulled; tied, gathered, adhered (FIG. 12A) or otherwise passed through (FIG. 12B) and about fiber 301 to shape loop segments 303 and provide the structure to matrix 300. Connecting segment 305 may extend beyond the effective length of fiber 301 thereby providing an extension 307 or handle which may be grasped by the clinician to facilitate placement and/or removal of the wound filler matrix 100 relative to the wound bed. The connecting segment 305 prevents the filament(s) and/or fibril(s) of the fiber from releasing from matrix 300 thereby minimizing the potential of the filaments remaining in the wound "w" upon removal of the material therefrom.

Wound filler matrix 300 may be severed at any predetermined longitudinal location to accommodate wounds of various sizes. With this arrangement, multiple size wounds may be accommodated with a single matrix 300. In addition, wound filler matrix 300 may be cut to provide a specific dimensioning to accommodate a specific wound type, e.g., for a tunneling or deep wound. It may be desirable to sever the matrix at a location along the longitudinal axis (e.g., location "k") such that a portion 305a of connecting segment 305 extends from the last loop. This may facilitate placement and/or subsequent removal of the reduced matrix segment 300a. Wound filler matrix 300 may be severed at several locations along the longitudinal axis "x" depending on the overall length of the wound filler matrix 300 provided and the wound type and/or size.

The fibers 301 of wound filler matrix 300 may be formed from mono- or multi-filaments 302. A monofilament, or a single strand of material of a sufficient thickness to be directly woven into matrix 300. A multifilament is more than one strand of material that has been twisted, bonded, or otherwise placed together to form a fiber as illustrated above in FIGS. 2A-2I. Each of the embodiments of fiber 301 depicted in FIGS. 13A-13I correspond to the multifilament arrangements of FIGS. 2A-2I, and may be arranged in the sinusoidal configuration depicted in FIG. 12 and attached via a connecting segment 305.

The filaments 102 of wound filler matrix 100 may take a wide variety of forms. Materials may be classified generally into two basic types including natural fibers and man-made fibers. Further, natural and man-made fibers include both absorbent and non-absorbent varieties as within the purview of those skilled in the art. Natural fibers are those produced by plants, animals and/or geologic processes. For example, natural fibers include vegetable fibers, which may be generated from arrangements of cellulose and bound together by lignin as in cotton, hemp, jute, flax, ramie and sisal, for example. Also, wood fibers are derived from tree sources and include groundwood, thermomechanical pulp (TMP) and bleached or unbleached kraft or sulfite (sulphite) pulps formed by a manufacturing process wherein lignin is removed to free the fibers from the wood structure. Animal fibers consist largely of proteins and include spider silk, sinew, catgut, wool and hair such as cashmere, mohair and angora, for instance. There are also mineral sources for natural fibers such as wollastinite, attapulgite, halloysite, and asbestos.

Man-made fibers include regenerated fibers and synthetic fibers. Regenerated fibers are those fabricated from natural materials by processing these materials to form a fiber structure. For example, regenerated fibers may be derived from the pure cellulose in cotton and wood pulp to form such products as Rayon and cellulose acetates. Fibers may also be regenerated from mineral sources such as glass or quartz to form fiberglass or optical fibers. Ductile metals such as copper, gold or silver may be drawn to form metallic fibers, and more brittle materials such as nickel aluminum or iron may be extruded or deposited.

Synthetic fibers are made entirely from synthetic materials such as petrochemicals, and are usually stronger than either natural or regenerated fibers. Synthetic fibers (as well as regenerated acetate fibers) tend to be thermoplastic, i.e., they are softened by heat. Therefore, these fibers may be shaped at high temperatures to add such features as pleats, creases and complex cross sections. Synthetic fibers may be formed from materials such as polyamide nylon, polyethylene terephthalatae (PET) or polybutylene teraphalate (PBT) polyester, phenol-formaldehyde (PF), polyvinyl alcohol (PVOH), polyvinyl chloride (PVC) and polyolefins such as polypropylene (PP) and polyethylene (PE).

Connecting segment 305 of wound filler matrix 300 may also take a wide variety of forms including the types and materials described above. Connecting segment 305 may be formed from the same or a different material as fiber 101.

Various suppliers may produce filaments as described above, as any commercial fiber or suture material may advantageously be employed in wound matrix 300. A nonexhaustive list of materials includes, but are not limited to, polymers and polymer blends selected from the group consisting of polyolefins (such as polyethylene and polypropylene including atactic, isotactic, syndiotactic, and blends thereof as well as, polyisobutylene and ethylene-alphaolefins copolymers, and fluorinated polyolefin such as polytetrafluoroethylene); polyesters (such as polyethylene terephthalate and polybutylene terephthalate); acrylic polymers and copolymers; modacrylics; vinyl halide polymers and copolymers (such as polyvinyl chloride); polyvinyl ethers (such as polyvinyl methyl ether); polyvinylidene halides (such as polyvinylidene fluoride and polyvinylidene chloride); polyacrylonitrile; polyvinyl ketones; polyvinyl aromatics (such as polystyrene); polyvinyl esters (such as polyvinyl acetate); copolymers of vinyl monomers with each other and olefins (such as etheylene-methyl methacrylate copolymers, acrylonitrile-styrene copolymers, ABS resins and ethylene-vinyl acetate copolymers); polyamides (such as nylon 4, nylon 6, nylon 6.6, nylon 610, nylon 11, nylon 12 and polycaprolactam); alkyd resins; polycarbonates; polyoxymethylenes; polyimides; polyethers; epoxy resins; aramids, polyurethanes; rayon; rayon-triacetate; and spandex.

Various polymer additives may be applied to individual mono- or multi-filaments 102, any of the filaments described above or a matrix 300 to enhance the healing of wound "w." For example, agents such as polyhexamethylene biguanide (PHMB) or other medicaments, antimicrobials, wound healing agents and wound debriding agents may be used to decrease the incidence of infection or otherwise promote healing of the wound "w." Such agents may include those agents for use in slow release treatments wherein the agent is released from the matrix material into the wound over time. Hydrolysis stabilizers may be incorporated to control the release of an agent or to maintain the integrity of the tow. Also, wetting agents may be applied to promote a moist wound environment.

Other additives may facilitate the removal of matrix 100 from the wound. For example, silicone or floropolymers such as PTFE may be added to provide filaments 102 with a slicker surface. A slicker surface may help allow the tow to conform comfortably to the shape of the wound "w." Still other additives may facilitate construction of the wound filler matrix 100 such as compatibilizers and adhesion promoters. Still other additives such as phase change materials, nanoparticles, UV-absorbers and sunblocks, stain resistant agents or flame retardants may find additional utility when in a wound matrix 300.

There are various types of manufacturing processes for the combination of multifilaments with one another to form the fiber. It may be convenient to supply each of the filaments to be combined coiled onto a spool to help provide the capability of continuous feeding of substantial lengths of the coiled filaments. The spools are normally mounted in an array which is commonly referred to as a creel. A creel may include a plurality of spindles projecting in a vertical direction from a base frame to accept spools with an internal void, such that the spools may spin about the spindles to pay out a length of the filament. Such a manufacturing process provides an opportunity to combine filaments to produce a tow with specific characteristics. One or more of the spools may simply be stocked with a filament having differing characteristics than other spools on the creel.

Filaments of differing denier per filament, e.g., 3, 11, or 18 denier per filament, may be combined to produce a fiber with a specific total denier, e.g., from about 1000 to about 10,000. The denier per filament may be conveniently adjusted to control fluid flow properties and the resiliency of matrix 100 when subject to application or removal pressure. Also, an exact number of filaments having a relatively low melting temperature may be incorporated into a creeling process to provide precise control over the adhesive properties that such filaments may provide when melted. Mixing of different polymers such as polypropylene with high tenacity PET is contemplated to control tow characteristics such as strength and wicking capability of a tow. A single filament or any number of filaments coated with an additive or healing agent described above may be incorporated into a fiber to promote healing of the wound "w." Any number of combinations of any of the filaments described above in any quantity may be assembled to produce a tow with the exact characteristics desired.

Also, other materials or similar materials arranged in a differing manner may be inserted into a fiber in a creeling process. For instance, porous membrane tubes may be inserted into or over a multifilament fiber to provide a bonding feature. Also twisted filaments, filaments with differing crimp patterns, or crimp patterns with differing spacing may be combined to form a fiber for use as matrix 300.

Various crimping and bulking methods are contemplated to permit the fiber of a tow to separate in areas such that the tow may receive and transport wound fluids. An air jet, or steam jet crimping process, or any of the crimping processes described above may be used to impart an S- or Z-type crimp to the fiber. These S- and Z-type crimps refer to a direction of crimping such that the crimped fiber form a zig-zag pattern that resembles either letter "S" or letter "Z."

Self crimping may be accomplished with an eccentric core-sheath arrangement of polymers described above with reference to FIG. 3B or a side-by-side arrangement as described with reference to FIG. 3C. Another option to produce a self crimping fiber is to combine full filaments of differing thermal characteristics in a creeling process. The crimped fiber may be opened, i.e., the loop segments of crimped fiber may be separated or spaced, to produce a particular texture or bulk. The loop segments of crimped fiber may be opened by air jets, or by longitudinal stretching and relaxing of the fiber with a threaded roll assembly.

An embodiment of the present disclosure comprises a multifilament fiber tow formed from primarily round cross section polypropylene filaments with a denier per filament from about 6 to about 10, e.g., about 8. The fiber may be crimped with either an S or Z-type crimp, and the loop segments may be lofted or opened by air jets or by stretching and relaxing. The fiber may be creeled from multi-filament yarns including a sufficient number of individual filaments to exhibit a yarn denier of about 300. About 100 spools of the about 300 denier yarns may be creeled to form a total tow denier of about 30,000. The yarns on about 30 of the spools may be treated with an antimicrobial such as PHMB, while the yarns on the remaining about 270 spools may be untreated. The fiber may be encapsulated in a spun polypropylene non-woven web to minimize the effect of loose filaments protruding from the tow. Alternatives include a similar fiber subject to air jet entanglement rather than encapsulation, and also a fiber in which substantially all of the yarns or filaments are treated with PHMB.

One-piece removal of such a tow from a wound "w" may be thus ensured where dressing material remaining in the wound "w" might otherwise go unnoticed.

Although the foregoing disclosure has been described in some detail by way of illustration and example, for purposes of clarity or understanding, it will be obvious that certain changes and modifications may be practiced within the scope of the appended claims. For example, it is envisioned that the wound filler matrix 300 may be used independent of the other components of the wound dressing 10 or may be used in combination with cover layer 22 and/or contact layer 18. Wound filler matrix 300 may be used as a wound bandage in the absence of negative pressure therapy, e.g., as a wound covering in a conventional application. Other uses are also envisioned.

What is claimed is:

1. A negative wound pressure therapy system, comprising:
a wound dressing configured to be placed over a wound, the wound dressing configured to form a substantially fluid-tight seal around the wound;
a material configured to be in fluid communication with a source of negative pressure, the material defining a length along a longitudinal axis and comprising at least one continuous fiber configured in a plurality of loop segments traversing the longitudinal axis and extending along the longitudinal axis, the material including a connecting segment extending along the longitudinal axis for substantially the same length as the plurality of loop segments, the connecting segment directly physically connected to two or more of the loop segments as the connecting segment extends along the longitudinal axis.

2. The system according to claim 1, wherein the connecting segment is connected to each loop segment.

3. The system according to claim 1, wherein the connecting segment is configured to be severed to provide a segment of the material.

4. The system according to claim 1, wherein the connecting segment is dimensioned to define a handle segment extending longitudinally beyond the at least one continuous fiber.

5. The system according to claim 1, wherein the connecting segment and the at least one continuous fiber comprise different material.

6. The system according to claim 1, wherein the at least one continuous fiber comprises multifilaments.

7. The system according to claim 1, wherein the at least one continuous fiber of the material is non-absorbent.

8. The system according to claim 1, wherein the at least one continuous fiber includes an additive.

9. The system according to claim 1, further comprising a wound contact layer.

10. The system according to claim 9, further comprising a cover layer.

11. The system according to claim 9, wherein the wound contact layer comprises a perforated film.

12. The system according to claim 1, further comprising the source of negative pressure configured to be in fluid communication with the wound dressing, the source of negative pressure configured to provide negative pressure to the wound.

* * * * *